United States Patent
Hu et al.

(10) Patent No.: US 12,083,088 B2
(45) Date of Patent: *Sep. 10, 2024

(54) SUBSTITUTED ESTERS CONTAINING POLYOLS AND SACCHARIDES FOR TREATING HEPATOTOXICITY AND FATTY LIVER DISEASES

(71) Applicant: SINEW PHARMA INC., Taipei (TW)

(72) Inventors: Oliver Yoa-Pu Hu, Taipei (TW); Tung-Yuan Shih, Taipei (TW); Cheng-Huei Hsiong, Taipei (TW); Hsin-Tien Ho, Taipei (TW)

(73) Assignee: SINEW PHARMA INC., Taipei (TW)

( * ) Notice: Subject to any disclaimer, the term of this patent is extended or adjusted under 35 U.S.C. 154(b) by 0 days.

This patent is subject to a terminal disclaimer.

(21) Appl. No.: 17/686,013

(22) Filed: Mar. 3, 2022

(65) Prior Publication Data

US 2022/0265587 A1    Aug. 25, 2022

Related U.S. Application Data

(62) Division of application No. 16/573,506, filed on Sep. 17, 2019, now Pat. No. 11,285,123, which is a division of application No. 15/564,526, filed as application No. PCT/CN2016/100187 on Sep. 26, 2016, now Pat. No. 10,456,371.

(60) Provisional application No. 62/222,959, filed on Sep. 24, 2015, provisional application No. 62/257,697, filed on Nov. 19, 2015.

(30) Foreign Application Priority Data

Mar. 31, 2016  (WO) ................ PCT/CN2016/078039

(51) Int. Cl.
| | | |
|---|---|---|
| A61K 31/225 | (2006.01) | |
| A61K 31/194 | (2006.01) | |
| A61K 45/06 | (2006.01) | |
| A61K 47/26 | (2006.01) | |
| A61P 1/16 | (2006.01) | |
| C07C 51/215 | (2006.01) | |
| C07C 69/42 | (2006.01) | |
| C07C 69/63 | (2006.01) | |
| C07D 319/06 | (2006.01) | |
| C07D 407/12 | (2006.01) | |
| C07H 13/04 | (2006.01) | |
| A61K 31/047 | (2006.01) | |
| A61K 31/428 | (2006.01) | |
| A61K 31/7004 | (2006.01) | |

(52) U.S. Cl.
CPC ............ *A61K 31/194* (2013.01); *A61K 45/06* (2013.01); *A61K 47/26* (2013.01); *A61P 1/16* (2018.01); *C07C 51/215* (2013.01); *C07C 69/42* (2013.01); *C07D 319/06* (2013.01); *C07D 407/12* (2013.01); *C07H 13/04* (2013.01); *A61K 31/047* (2013.01); *A61K 31/428* (2013.01); *A61K 31/7004* (2013.01); *A61K 2300/00* (2013.01)

(58) Field of Classification Search
CPC .............................. A61K 31/225; C07C 69/63
USPC ............................................... 514/506; 560/1
See application file for complete search history.

(56) References Cited

U.S. PATENT DOCUMENTS 4,661,519 A    4/1987  Shiga et al.

FOREIGN PATENT DOCUMENTS

WO    WO 2017/050298 A1    3/2017

OTHER PUBLICATIONS

CAS Registry Database, RN: 19455-97-1, RN: 87900-80-9, entered STN: Nov. 16, 1984, accessed on Jun. 25, 2020.
Dörwald, "Side reactions in Organic Synthesis: a guide to successful synthesis design," Weinheim: WILEY-VCH, Verlag GmbH & Co. KGaA, 2005, preface, 6 pages.
Hackam et al., "Translation of research evidence from animals to humans," JAMA, vol. 296, No. 14, Oct. 11, 2006, pp. 1731-1732.
Jordan, "Tamoxifen: a most unlikely pioneering medicine," Nature Reviews: Drug discovery, vol. 2, Mar. 2003, pp. 205-213.
U.S. Appl. No. 16/573,506, filed Sep. 17, 2019.
U.S. Appl. No. 15/564,526, filed Oct. 5, 2017.

*Primary Examiner* — Douglas M Willis
(74) *Attorney, Agent, or Firm* — Birch, Stewart, Kolasch & Birch, LLP

(57) ABSTRACT

Compounds are of the structure of Formula (II)

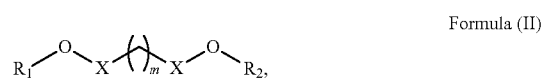

Formula (II)

wherein: each X is —C(=O)—; $R_1$ is a $C_1$-$C_{18}$ alkyl polyol; $R_2$ is a saccharide group of formula $(G)_p$; G is a monosaccharide residue, where (i) at least one of the —OH groups in $(G)_p$ is substituted by a halogen atom, and (ii) the saccharide group of formula $(G)_p$ is linked to —O— through a —$CH_2$ group; p is 1 or 2; and m is 1, 2, 3, 4, 5, 6, 7, 8, 9 or 10. The compounds are effective in treating hepatotoxicity and fatty liver diseases.

81 Claims, 6 Drawing Sheets

A linker agent that can provide one or more –COOH    +    R-OH
to perform esterification The linker agent in the first esterification provides
the first –COOH to form a first ester bond with R Step 1
1st esterification

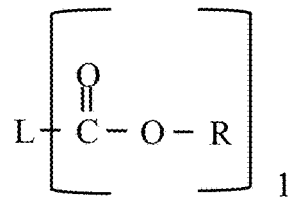
1

The linker agent in the second esterification provides
the second–COOH to form a second ester bond with R Step 2
2nd esterification

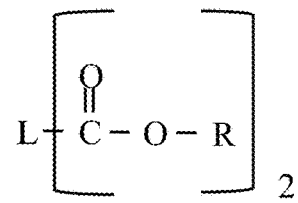
2

The linker agent in the second esterification provides
the third –COOH to form a third ester bond with R Step 3
3rd esterification

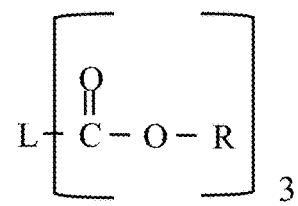
3

The linker agent in the second esterification provides
the fourth –COOH to form a fourth ester bond with R Step 4
4rd esterification

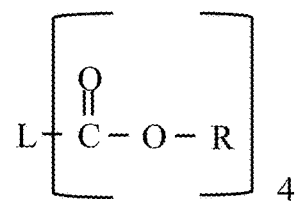
4

Fig. 6

SUBSTITUTED ESTERS CONTAINING POLYOLS AND SACCHARIDES FOR TREATING HEPATOTOXICITY AND FATTY LIVER DISEASES

RELATED APPLICATION

This application is a Divisional of U.S. application Ser. No. 16/573,506, filed Sep. 17, 2019, which is a Divisional of U.S. application Ser. No. 15/564,526, filed Oct. 5, 2017 (now U.S. Pat. No. 10,456,371 issued on Oct. 29, 2019), which is the National Phase of PCT International Application No. PCT/CN2016/100187, filed on Sep. 26, 2016, which claims priority under 35 U.S.C. 119(e) to U.S. Provisional Application No. 62/222,959, filed on Sep. 24, 2015 and 62/257,697, filed on Nov. 19, 2015 and under 35 U.S.C. 119(a) to Patent Application No. PCT/CN2016/078039, filed in China on Mar. 31, 2016, all of which are hereby expressly incorporated by reference into the present application.

TECHNOLOGY FIELD

The present invention relates to compounds effective in treating hepatotoxicity and fatty liver diseases and uses thereof.

BACKGROUND OF THE INVENTION

Injuries in organs may be caused by toxic agents such as a therapeutic drug when administered overdose which often leads to injuries in organs especially liver or kidney. Acetaminophen (also known as Panadol) is also called paracetamol or N-acetyl-para-aminophenol (APAP) and is the most widely used pain-relieving and fever-reducing drug on the market. Each year, numerous cases of drug intoxication or suicide are reported due to improper use of APAP, and liver damage caused by APAP is the main cause of severe diseases and death. Alcohols or organic solvents such as carbon tetrachloride ($CCl_4$) may also cause hepatotoxicity. A number of clinical studies have demonstrated that hepatotoxicity induced by APAP is preventable and early diagnosis along with real-time administration of the antidote N-acetylcysteine (NAC) can prevent the occurrence of hepatotoxicity.

Early detection of acetaminophen overdose is necessary because the best prognosis can be achieved if the antidote is given within 8 hours after poisoning. The early signs of drug intoxication include discomfort, nausea and vomiting. However, some patients may show no signs of intoxication at the early stage (stage 1) even if their blood concentrations of acetaminophen are at the poisoning levels and their abnormal liver function is apparently abnormal. The signs of hepatotoxicity, such as abdominal pain, persistent vomiting, jaundice, right upper quadrant pain, usually become apparent 24-48 hours after ingestion of a significant amount of acetaminophen (stage 2). Serum amintransferase usually starts to rise 16 hours after administration with clinical symptoms. Stage 3 usually occurs 3-4 days after administration and the degree of liver damage as well as prognosis can be well predicted at the time. The signs of hepatotoxicity progress from mild symptoms with elevated liver function values (AST>1,000 IU/L) to severe acute fulminant hepatitis accompanied by metabolic acidosis, jaundice, hyperglycemia, AST>1,000 IU/L, abnormal blood clotting and hepatic/brain lesions. Stage 4 will cause oliguria renal failure or death in severe cases.

Some patients with acetaminophen intoxication show only mild liver damage but with severe renal toxicity which is mainly caused by direct metabolism of APAP in P-450s (cytochrome P450s, CYPs) of the renal tubule. Nonetheless, acute renal failure may also result from hepatorenal syndrome caused by acute liver failure and the fraction excretion of Na (FeNa) can be used for differentiation primary renal damage (FeNa>1) from hepatorenal syndrome (FeNa>1). The calculation formula for FeNa is (Sodium urinary÷Creatinine urinary)÷(Sodium plasma+Creatinine plasma)×100.

The peak concentration of acetaminophen in blood is achieved 1-2 hours after oral administration and a significant amount is eliminated by liver, more than 90% is conjugated to glucuronide and sulfate and form non-toxic metabolites and only less than 5% is eliminated by different CYPs, including CYP2E1, CYP1A2 and CYP3A4, and among which CYP2E1 and CYP1A2 are the major enzymes for metabolism. The metabolite produced by these enzymes, N-acetyl-p-benzoquinoneimine (NAPQI) is a very active electrophile. Under normal conditions, NAPQI will react immediately with glutathione in the cell and form non-toxic mercaptide. Overdose of acetaminophen makes the consumption rate of glutathione greater than its synthesis rate and when the glutathione level of the cell is lower than the normal range of 30%, NAPQI will bind to large molecules or nucleic acids containing cysteine and lead to liver damage. From histochemical stains, NAPQI will bind to the thiol group of cysteine and form a covalent bond in centrilobular areas before occurrence of liver cell necrosis.

Patients with liver disease, alcohol addiction or who are taking drugs which may induce the activity of P450 such as carbamazepine, ethanol, Isoniazid, Phenobarbital (may be other barbiturates), Phenytoin, Sulfinpyrazone, Sulfonylureas, Rifampin and Primidone are the susceptible groups of developing severe hepatotoxicity caused by APAP and may easily die if the patient also develops complications such as adult respiratory distress syndrome, cerebral edema, uncontrollable bleeding, infection or Multiple organ dysfunction syndrome (MODS). Take alcohol for example, alcohol is mainly eliminated by CYP2E1 of liver and its mechanism of APAP intoxication is divided into three stages: at the first stage alcohol competes the receptors for CYP2E1 with APAP in the liver and the concentration of NAPQI will reduce during the stage, at the second stage alcohol prolongs the half-life of CYP2E1 from 7 hours to 37 hours which increases the level of CYP2E1 in the liver and the concentration of NAPQI will slowly increase during this stage, and at the third stage, during alcohol withdrawal, more CYP2E1 is found in the liver to eliminate acetaminophen and consequently the toxic metabolites of acetaminophen increases significantly and lead to liver damage. Recent studies have shown that diallyl sulfide can effectively prevent hepatotoxicity caused by acetaminophen in mice and further demonstrated diallyl sulfide can inhibit the activity of CYP2E1. It is speculated that the protection mechanism of diallyl sulfide against hepatotoxicity induced by acetaminophen is by inhibition of the production of the intermediate NAPQI from acetaminophen. Previous studies have suggested by inhibition the consumption of reduced glutathione in liver cells, oxidation activation, mitochondrial dysfunction and DNA damage caused by NAPQI can be reduced and subsequently minimize liver damage induced by acetaminophen. For example, *Panax notoginseng*, adenosine and its derivatives adenosine monophosphate, adenosine diphosphate and adenosine triphosphate can prevent liver damage induced by acetaminophen through this protection mechanism.

Fatty liver is considered another factor leading to liver damages. Under normal circumstances, fat accounts for 3% by weight of the liver. Clinically, "fatty liver disease (FLD)" means fat in the liver exceeds 5% by weight of the liver, or more than 10% of the liver cells show vesicular fatty changes in the liver tissue sections. According to the causes of diseases, fatty liver can be divided into alcoholic fatty liver diseases (AFLD), non-alcoholic fatty liver diseases (NAFLD), or other fatty liver diseases derived from other factors, such as drugs. Fatty liver diseases are pathologically characterized by the appearance of fatty metamorphosis or steatosis, steatohepatitis, or the like. By the percentage of liver cells suffering from steatosis, fatty liver is categorized as mild (<33%), moderate (33-66%) and severe (>66%). Previously, fatty liver was considered a benign and reversible condition, and thus less taken seriously, but recent studies had found that it will lead to severe liver fibrosis and cirrhosis, and even liver cancer. As the population of obese people increases, the prevalence of FLD also increases.

The main cause of liver diseases in European and American countries is due to chronic excessive drinking, therefore, the vast majority of liver diseases are caused by alcohol lesions. But over the past 15-20 years, NAFLD has become the first cause of diseases to be considered for liver dysfunction in European and American countries. Thaler had ever described NAFLD in 1962. In 1980, Ludwig proposed "Non-alcoholic steatohepatitis (NASH)" from accompanying NAFLD he found in a group of obese female patients with diabetes and hyperlipidemia. Thereafter, in 1986, Schaffner emphasized again that NASH played an important role in the mechanism of fibrosis derivation in the course of NAFLD. Until 1998, Day found that 15-50% of patients with NASH were suffered from different degrees of fibrosis derivation, so clinicians started to pay attention to NAFLD. Today, in addition to AFLD, NASH is not just a stage in the natural progression of NAFLD in clinical practice. Due to the presence of NASH, NAFLD is no longer considered a benign liver disease.

Regarding the mechanism of NAFLD, Day and James in the United Kingdom proposed Two-hit hypothesis based on a large number of clinical researches and animal experiments. Fatty liver occurs upon the first hit, and steatohepatitis occurs upon the second hit. The first hit is prompted by excessive accumulation of fat in the liver, which is caused by obesity, hyperlipidemia, etc. The second hit is due to oxidative stress and the effect of reactive oxygen species (ROS) in mitochondria, resulting in lipid peroxidation on the liver cell membrane, release of original inflammatory cytokines and free radicals, and fibrosis due to activation of stellate cells, and leading to liver cell necrosis. The mechanism of NASH involves the peroxidation of triglyceride, oxidative stress, ROS response, increased peroxidation of lipids in liver cells, or increase of cytokines and liver enzymes, leading to a series of autoimmune interactions.

The causes of fatty liver are mostly associated with long-term excessive intake of animal fat, protein, carbohydrates, excess calories transforming into fat accumulated in the body, leading to obesity and fatty liver. Patients with fatty liver may have normal blood GOT/GPT values. Therefore, a correct diagnosis of fatty liver must use the abdominal ultrasound, which currently provides more than 97% accuracy.

Currently, there is no ideal drug providing specific therapeutic effects for FLD, the treatment guidelines of which aim at improving the potential risk factors or controlling the progress of chronic diseases by using drugs. It is recommended to apply symptomatic treatments according to the causes of fatty liver. For example, those who suffering from fatty liver caused by overweight should lose weight moderately. Anyone with alcoholic fatty liver needs to quit drinking and eats a balanced diet for improving the conditions. Chemicals or drugs that damage liver and lead to fatty liver diseases through long-term contact shall immediately be stopped using. Fatty liver caused by diseases, such as hepatitis C, high blood fat, etc., shall be treated by treating the original diseases, such as treating hepatitis C or controlling blood lipids. However, if excessive triglycerides are due to personally physical factors, it is hard to ameliorate fatty liver diseases by losing weight.

However, the current drugs that are commonly used in clinical to lower serum triglycerides and cholesterol are often accompanied with side effects, for example, hepatotoxicity, myopathy such as myalgia, myositis, rhabdomyolysis, and the like. Regarding the lipid-lowering drugs, muscle toxicity is the most notable side effect. Especially, Statins shows the highest occurrence of muscle toxicity, and fibric acid follows. In addition, the lipid-lowering drugs have a "fat driving" effect, which "drives" blood lipids to the liver, where fat accumulation already exists and the influx of lipids is difficult to be processed, leading to excessive accumulation of fat in the liver and making fatty liver worse. It can be seen that the lipid-lowering drugs are not suitable for the treatment of FLD.

BRIEF SUMMARY OF THE INVENTION

In one aspect, the present invention provides new compounds, the structure of which is represented by Formula (I) as follows Formula (I)

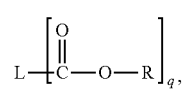

wherein

L is a saturated or unsaturated aliphatic group;

R is selected from the group consisting of hydrogen, a polyol group and a saccharide group of $(G)_p$ wherein G is a monosaccharide residue and p is an integer from 1 to 100 wherein at least one of the hydroxyl groups in $(G)_p$ is substituted by a halogen atom; and Q is an integer from 2 to 4, and each of R is the same or different, or a pharmaceutically acceptable salt thereof.

In some embodiments, the compounds of the present invention are represented by Formula (II) as follows:

    Formula (II), wherein

X is C=O;

$R_1$ and $R_2$ are the same or different, selected from the group consisting of hydrogen, a polyol group and a saccharide group of (G), wherein G is a monosaccharide residue and p is an integer from 1 to 100 wherein at least one of the hydroxyl groups in $(G)_p$ is substituted by a halogen atom, wherein when $R_1$ is hydrogen, then $R_2$ is not hydrogen; and m is an integer from 1 to 40.

In another aspect, the present invention provides a pharmaceutical composition comprising at least one of the compounds as described herein or a pharmaceutically acceptable salt thereof together with a pharmaceutically acceptable carrier.

In still another aspect, the present invention provides a treatment method by administering to a subject in need an effective amount of at least one of the compounds as described herein or a pharmaceutically acceptable salt thereof.

In some embodiments, the method of the present invention is provided to prevent or treat a disease or condition characterized by increased cytochrome P450 activities or increased free radical levels in a subject in need thereof.

In some embodiments, the method of the present invention is provided to prevent or treat organ injuries in a subject in need.

In some embodiments, the method of the present invention is provided to prevent or treat hepatotoxicity in a subject in need.

In some embodiments, the method of the present invention is provided to prevent or treat fatty liver, protect liver function or ameliorate liver diseases caused by fatty liver or other associated disorders.

In yet another aspect, the present invention provides use of the compounds as described herein or a pharmaceutically acceptable salt thereof for manufacturing a medicament. In particular, the medicament is useful in preventing or treating (i) a disease or condition characterized by increased cytochrome P450 activities or increased free radical level, (ii) organ injuries, and/or (iii) hepatotoxicity, and/or (iv) preventing or treating fatty liver, protecting liver function or ameliorating liver diseases caused by fatty liver or other associated disorders.

The details of one or more embodiments of the invention are set forth in the description below. Other features or advantages of the present invention will be apparent from the following detailed description of several embodiments, and also from the appending claims.

BRIEF DESCRIPTION OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

In the drawings:

FIG. 6 shows a general scheme of synthesis process of the compound of the present invention.

DETAILED DESCRIPTION OF THE INVENTION

Figure 1:
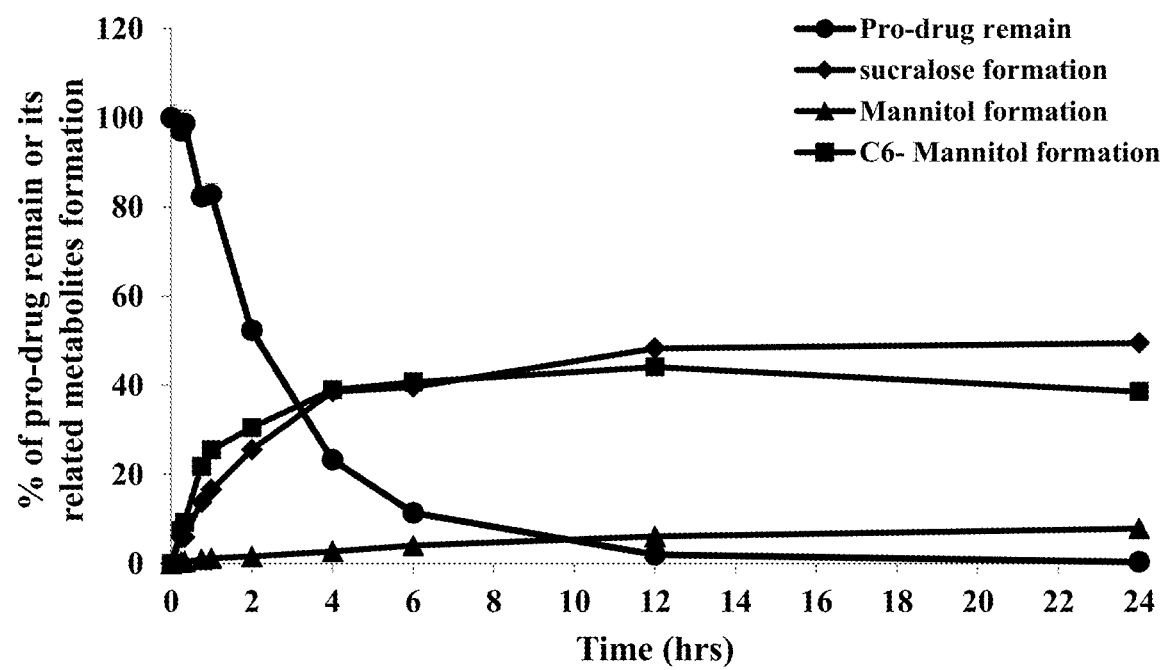
FIG. 1 shows the percentage of pro-drug remain or its related metabolites formation in blood (in vitro).

Unless defined otherwise, all technical and scientific terms used herein have the same meanings as is commonly understood by one of skill in the art to which this invention belongs.

As used herein, the articles "a" and "an" refer to one or more than one (i.e., at least one) of the grammatical object of the article. By way of example, "an element" means one element or more than one element.

I. Compounds

In one aspect, the present invention provides new compounds, the structure of which is represented by Formula (I) as follows

Formula (I)

wherein

L is a saturated or unsaturated aliphatic group;

R is selected from the group consisting of hydrogen, a polyol group and a saccharide group of $(G)_p$ wherein G is a monosaccharide residue and p is an integer from 1 to 100 wherein at least one of the hydroxyl groups in $(G)_p$ is substituted by a halogen atom; and Q is an integer from 2 to 4, and each of R is the same or different, or a pharmaceutically acceptable salt thereof.

The term "aliphatic" or "aliphatic group", as used herein, denotes a hydrocarbon moiety that may be straight-chain (i.e., unbranched), branched, or cyclic (including fused, bridging, and spiro-fused polycyclic) and may be completely saturated or may contain one or more units of unsaturation, but which is not aromatic. In general, aliphatic groups contain 1-40 carbon atoms. In some embodiments, aliphatic groups contain 1-20 carbon atoms, or 1-12 carbon atoms, 1-8 carbon atoms, or 1-4 carbon atoms. In some embodiments, aliphatic groups contain 3-20 carbon atoms, or 3-12 carbon atoms, 3-8 carbon atoms, or 3-4 carbon atoms. Suitable aliphatic groups include, but are not limited to, linear or branched, alkyl, alkenyl, and alkynyl groups, and hybrids thereof such as (cycloalkyl)alkyl, (cycloalkenyl)alkyl or (cycloalkyl)alkenyl.

In certain embodiments, the L group in Formula (I) is selected from (a) a straight alkyl group, (b) a branched alkyl group, (c) a straight alkyl group substituted with a benzene ring, (d) a branched alkyl group substituted with a benzene ring, (e) a benzenyl group where the benzene ring contains a straight chain aliphatic group, and (f) a benzenyl group where the benzene ring contains a branch chain of aliphatic group.

The term "polyol group", as used herein, denotes an alcohol containing multiple hydroxyl groups (two or more hydroxyl groups) per molecule. In particular, the polyol group can be linear or circular, substituted or unsubstituted, or mixtures thereof, so long as the resultant complex is water-soluble and pharmaceutically acceptable.

In some embodiments, the polyol group is a C3-24 polyol, particularly, a C3-20 polyol, more particularly, a C3-12 polyol, or a C3-12 polyol, containing 2 or more hydroxyl groups.

In more particular embodiments, the polyol group is represented by —CH—(CHOH)$_n$CH$_2$OH wherein n is 1-22, 1-18, 1-10, or 1-6. In one certain example, n is 4.

Preferred polyols are sugar alcohols. Examples of polyols include, but are not limited to, 3-carbon polyols (e.g. glycerol, erythritol and threitol); 5-carbon polyols (e.g. arabitol, xylitol and ribitol); 6-carbon polyols (e.g. mannitol, sorbitol, galactitol, fucitol, iditol and inositol); 12-carbon polyols (e.g. volemitol, isomalt, maltitol and lactitol); 18-carbon polyols (e.g. maltotriitol); and 24-carbon polyols (maltotetraitol).

In Formula (I), G represents a monosaccharide residue. The monosaccharide as used herein is preferably a 6-carbon monosaccharide having the chemical formula C$_6$H$_{12}$O$_6$ (i.e. hexose). The hexose may be in the D configuration, the L configuration, or a combination thereof. Hexoses are typically classified by functional groups. For example, aldohexoses have an aldehyde at position 1 such as allose, altrose, glucose, mannose, gulose, idose, galactose, and talose; and ketohexoses have a ketone at position 2 such as psicose, fructose, sorbose, and tagatose. A hexose also contains 6 hydroxyl groups and the aldehyde or ketone functional group in the hexose may react with neighbouring hydroxyl functional groups to form intramolecular hemiacetals or hemiketals, respectively. If the resulting cyclic sugar is a 5-membered ring, it is a furanose. If the resulting cyclic sugar is a 6-membered ring, it is a pyranose. The ring spontaneously opens and closes, allowing rotation to occur about the bond between the carbonyl group and the neighbouring carbon atom, yielding two distinct configurations (a and B). The hexose may be in either the S configuration or the R configuration.

According to the present invention, at least one of the hydroxyl groups in the one or more monosaccharide residues in formula (I) is substituted by a halogen atom. Examples of the halogen atom includes chlorine, bromine and iodine. Specifically, the halogen atom is chlorine.

As used herein, the term "S" or "R" is a way to name an optical isomer by its configuration, without involving a reference molecule, which is called the R/S system. It labels each chiral center R or S according to a system by which its ligands are each assigned a priority, according to the Cahn Ingold Prelog priority rules, based on atomic number. This system labels each chiral center in a molecule (and also has an extension to chiral molecules not involving chiral centers). If the compound has two chiral centers, it can be labeled, for example, as an (S,S) isomer versus an (S,R) isomer.

As used herein, the term "pharmaceutically acceptable salt" includes acid addition salts. "Pharmaceutically acceptable acid addition salts" refer to those salts which retain the biological effectiveness and properties of the free bases, which are formed with inorganic acids such as hydrochloric acid, hydrobromic acid, sulfuric acid, nitric acid, phosphoric acid and the like, and organic acids such as acetic acid, propionic acid, pyruvic acid, maleic acid, malonic acid, succinic acid, fumaric acid, tartaric acid, citric acid, benzoic acid, mandelic acid, methanesulfonic acid, ethanesulfonic acid, p-toluenesulfonic acid, salicylic acid, trifluoroacetic acid and the like.

In some embodiments, in Formula (I), q is 2, 3 or 4, at least one of the R group is different from another one of R.

In certain embodiments, in Formula (I), q is 2.

In such embodiments, the compound of the present invention can be represented by Formula (II) as follows:

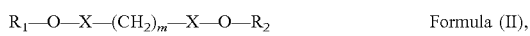

$R_1$—O—X—(CH$_2$)$_m$—X—O—$R_2$    Formula (II), wherein

X is C=O;

$R_1$ and $R_2$ are the same or different, selected from the group consisting of hydrogen, a polyol group and a saccharide group of (G)$_p$ wherein G is a monosaccharide residue and p is an integer from 1 to 100 wherein at least one of the hydroxyl groups in (G)$_p$ is substituted by a halogen atom, wherein when $R_1$ is hydrogen, then $R_2$ is not hydrogen; and m is an integer from 1 to 40.

or a pharmaceutically acceptable salt thereof.

In certain embodiments, in Formula (II), $R_1$ is the polyol group and $R_2$ is the saccharide group of (G)$_p$. In such case, the compound of Formula (II) is deemed as a conjugate of the polyol moiety linked to the sugar moiety by a linker via ester bonds. In particular, the linker is represented by —O—X—(CH$_2$)$_m$—X—O— (Formula (L)) wherein X is C=O and m is 1-40, 1-20, 1-12, 1-8 or 1-4, more particular, m is 3-20, 3-12, 3-8 or 3-4. In one certain example, m is 4.

In some embodiments, p is 2. The saccharide group is represented by -G$_1$-O-G$_2$, wherein G$_1$ and G$_2$ are the same or different, selected from the group consisting of an aldohexose and a ketohexose, and at least one of the hydroxyl groups in G$_1$ or at least one of the hydroxyl groups in G$_2$ is substituted by a halogen atom.

In some embodiments, G$_1$ is glucose wherein one of the hydroxyl groups is substituted by chlorine; and G$_2$ is fructose wherein two of the hydroxyl groups are substituted by chlorine.

In certain embodiments, the saccharide group is represented by formula (Ia)

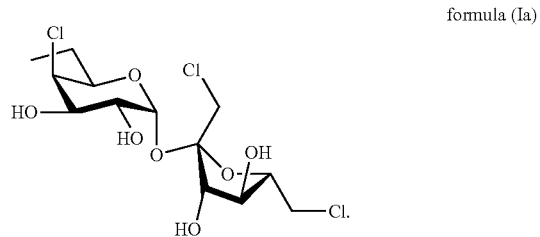

formula (Ia)

Certain examples of the compound of the present invention are as follows: ((2R,3R,4R,5R,6R)-6-(((2R,5R)-2,5-bis (chloromethyl)-3,4-dihydroxytetrahydro furan-2-yl)oxy)-3-chloro-4,5-dihydroxytetrahydro-2H-pyran-2-yl)methyl ((2R,3R,4R)-2,3,4,5,6-pentahydroxyhexyl) adipate Formula 1

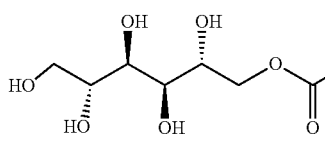
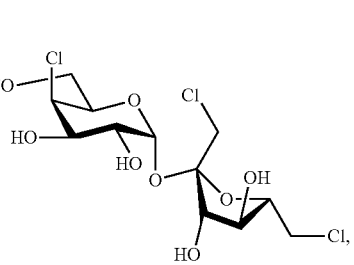

and
C6-mannitol of Formula 2

Formula 2

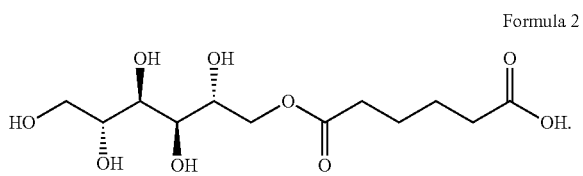 [SMILES: O=C(O)CCCCC(=O)OC[C@@H](O)[C@@H](O)[C@H](O)[C@H](O)CO]

In another aspect, the present invention provides an intermediate of Formula C as follows:

C

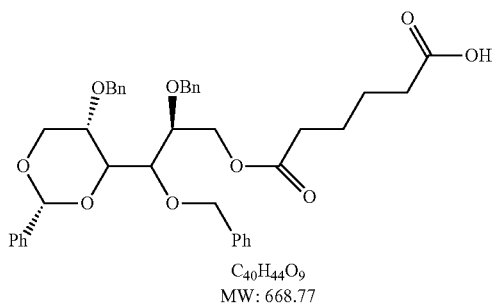

$C_{40}H_{44}O_9$
MW: 668.77 wherein Ph is phenyl and Bn is benzyl.

The compound of Formula (I) can be chemically synthesized for example by a process as shown in the general scheme of FIG. 6.

In particular, a linker agent that can provide one or more-COOH group to perform esterification with an alcohol is provided. In step 1, the linker agent providing a first-COOH group (others if available are protected) reacts with R having a first free hydroxyl group (others if available are protected) to proceed with the first esterification, producing the compound of Formula (I) where q is 1. In step 2, the linker agent providing a second-COOH group (others if available are protected) reacts with R having a second free hydroxyl group (others if available are protected) to proceed with the second esterification, producing the compound of Formula (I) where q is 2. In step 3, the linker agent providing a third-COOH group (others if available are protected) reacts with R having a third free hydroxyl group (others if available are protected) to proceed with the third esterification, producing the compound of Formula (I) where q is 3. In step 4, the linker agent providing a fourth-COOH group (others if available are protected) reacts with R having a fourth free hydroxyl group (others if available are protected) to proceed with the third esterification, producing the compound of Formula (I) where q is 4.

In some embodiments, the linker agent to perform the esterification is represented by Formula (La)

$$P_1\text{—O—X—}(CH_2)_m\text{—X—O-}P_2 \qquad \text{Formula (La)}$$

wherein X and m are as defined above, and $P_1$ and $P_2$ are the same or different and are a protecting group or H.

In some embodiments, the linker agent to perform the esterification is represented by Formula (La)

Formula (Lb)

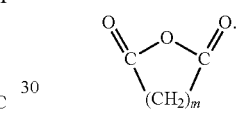

As used herein, a "protecting group" is a chemical group that is attached to a functional moiety (for example to the oxygen in a hydroxyl group or the nitrogen in an amino group, replacing the hydrogen) to protect the functional group from reacting in an undesired way. A protecting group includes, for example, t-butyl group, a cycloalkyl group (e.g., cyclohexyl group), an aryl group (e.g., 2,4-dinitrophenyl group), an aralkyl group (e.g., benzyl group, 2,6-dichlorobenzyl group, 3-bromobenzyl group, 2-nitrobenzyl group, 4-dimethylcarbamoylbenzyl group, and triphenylmethyl group), a tetrahydropyranyl group, an acyl group, an alkoxycarbonyl group (e.g., t-butoxycarbonyl group), an aralkyloxycarbonyl group (e.g., benzyloxycabonyl group, 2-bromobenzyloxycarbonyl group), a dialkylphosphinothioyl group (e.g., dimethylphosphinothioyl group) and a diarylphosphinothioyl group (e.g., diphenylphosphinothioyl group). A preferred protecting group includes an acyl group and the like.

In one certain example, Scheme 1 is provided in Example 1 showing the particular synthesis process of the compound of the present invention.

II. Uses of the Compounds of the Present Invention

The compounds of the invention can be used as a medicament for treatment methods. In general, the compound of Formula (1) acts as a prodrug that after administration can turn into metabolites providing therapeutic effects as needed as described herein. In one example, the compound of Formula (I) is compound F, which after administration can turn into mannitol, sucralose and C6-mannitol, all of which can act as P450 inhibitors and provide anti-hepatotoxicity effects, for example. See examples below.

The present invention provides a treatment method by administering to a subject in need an effective amount of at least one of the compounds as described herein or a pharmaceutically acceptable salt thereof.

It is found that compounds of the invention are effective as P450 inhibitors, for example.

In some embodiments, the method of the present invention is provided to prevent or treat a disease or condition characterized by increased cytochrome P450 activities in a subject in need thereof.

Examples of such diseases or conditions are listed in Table A.

TABLE A

Diseases

| | |
|---|---|
| alcoholic hepatitis | hepatoblastoma |
| drug-induced hepatitis | Liver, renal chronic disease |
| alcoholic liver cirrhosis | obesity |
| liver disease | poisoning |
| liver cirrhosis | insulin resistance |
| alcohol abuse | chronic liver disease |
| isoniazid toxicity | hepatitis chronic |
| nonalcoholic steatohepatitis | renal disease |
| tuberculosis | inflammation |
| Hepatitis | alcohol withdrawal |
| Fatty liver disease | alcoholic cirrhosis |
| Hepatocellular carcinoma | liver damage |
| liver diseases alcoholic | alcoholism |
| hepatitis halothane | hepatitis toxic |
| fatty liver alcoholic | |
| fatty liver | hepatic necrosis |
| alcohol-related disorders | cirrhosis |
| cerebrovascular disease | acute alcoholic hepatitis |
| coronary artery disease | Liver, renal histopathology |
| Liver, renal cell damage | Ethanol-induced and obesity-induced oxidant stress and liver injury |
| Liver, renal necrosis | heavy metal poisoning |
| hepatitis c chronic | liver fibrosis |
| cardiovascular disease | atherosclerosis |

In some embodiments, the method of the present invention is provided to prevent or treat a disease or condition characterized by increased free radical levels in a subject in need thereof.

In some embodiments, the method of the present invention is provided to prevent or treat organ injuries in a subject in need.

In particular examples, the organ injuries are in liver or kidney.

In particular examples, organ injuries or hepatotoxicity are caused by a therapeutic drug, $CCl_4$ or lipid accumulation.

In particular examples, the therapeutic drug is acetaminophen.

In some embodiments, the method of the present invention is provided to prevent or treat hepatotoxicity in a subject in need.

In some embodiments, the method of the present invention is provided to prevent or treat fatty liver, protecting liver function or ameliorating liver diseases caused by fatty liver or other associated disorders.

As used herein, the term "liver fat content" refers to the content of fat that is accumulated in the liver of a subject and includes broadly defined lipids, such as triglyceride (TG) and cholesterol. As used herein, the term "reducing liver fat content" generally refers to the reduction of the content of abnormal liver fat in a subject, i.e. to decrease the content of abnormal liver fat and, more particularly, to lower the content of abnormal liver fat to normal level. For example, under normal circumstance, fat accounts for 3% by weight of the liver. If fat in the liver exceeds 5% by weight of the liver, it is determined as abnormal fat accumulation (the liver fat content described above is a relative percentage for exemplification, and may vary due to ethnicity and other factors). In a specific aspect, the term "reducing liver fat content" used herein could means that the content of abnormal liver fat in a subject is reduced, for example, from 5% by weight of the liver or more to 3% by weight of the liver. Liver fat content can be assessed by standard analytical methods, including but not limited to ultrasound analysis, magnetic resonance imaging (MRI), magnetic resonance spectroscopy (MRS), computed tomography (CT), and liver biopsy.

As used herein, the term "liver function" refers to one or more physiological functions performed by the liver. Liver function can be analyzed by a lot of conventional assays, such as alanine aminotransferase (ALT) analysis or aspartate transaminase (AST) analysis. According to the present invention, the compound described herein can be used to maintain the liver function, including improvement of the liver function and preventing the liver from damage.

As used herein, the term "liver diseases" refers to liver cell injury or damage caused by certain factors, which then potentially lead to liver dysfunction. According to the present invention, the compound proposed herein can be used to ameliorate liver diseases caused by fatty liver in some embodiments. More particularly, "liver damage" used herein refers to liver with histological or biochemical dysfunction, as compared with normal liver. In a specific embodiment, "liver damage" refers to liver lesions caused by alcoholic or non-alcoholic factors, such as high fat diet or obesity, or therapeutic drugs or organic solvents. In a specific embodiment, "liver damage" can be liver tissue damage with one or more characteristics selected from steatosis, lobular inflammation, hepatocyte ballooning, and vesicular fat droplets produced by liver cells. In a specific embodiment, "liver damage" can be biochemical dysfunction of liver, which can be determined from the activity of alanine aminotransferase (ALT) or aspartate transaminase (AST). Higher activity of ALT or AST indicates severer dysfunction of liver's biochemical function.

As used herein, the term "liver antioxidant activity" refers to the activity or ability against oxidative stress. Improvement of liver antioxidant activity of a subject by the compound according to the present invention refers to, includes, but is not limited to reducing oxidative stress or enhancing enzyme activity or content of the members of antioxidant systems. The members of antioxidant systems may be glutathione peroxidase (GPx), glutathione (GSH), glutathione reductase (GRd), and/or superoxide dismutase (SOD).

According to the present invention, the compound described herein includes common excipients and bioflavonoids, which may be used to reduce liver fat content and ameliorate associated disorders. The term "associated disorders" described herein includes the disorders caused by abnormal accumulation of liver fat and including, but not limited to fatty liver diseases, acute and chronic alcoholic fatty liver diseases, acute and chronic non-alcoholic fatty liver diseases, acute and chronic alcoholic hepatitis, acute and chronic non-alcoholic steatohepatitis, non-alcoholic cirrhosis and alcoholic cirrhosis (ICD-9-CM Diagnosis Codes: 571.8, 571.0, 571.1, 571.2, 571.3, 571.4, 571.5, 571.9).

As used herein, the term "preventing" refers to the preventive measures for a disease or the symptoms or conditions of a disease. The preventive measures include, but are not limited to applying or administering one or more active agents to a subject who has not yet been diagnosed as a patient suffering from the disease or the symptoms or conditions of the disease but may be susceptible or prone to the disease. The purpose of the preventive measures is to avoid, prevent, or postpone the occurrence of the disease or the symptoms or conditions of the disease.

As used herein, the term "treating" refers to the therapeutic measures to a disease or the symptoms or conditions of a disease. The therapeutic measures include, but are not limited to applying or administering one or more active agents to a subject suffering from the disease or the symptoms or conditions of the disease or exacerbation of the disease. The purpose of the therapeutic measures is to treat, cure, mitigate, relieve, alter, remedy, ameliorate, improve, or affect the disease, the symptoms or conditions of the disease, disability caused by the disease, or exacerbation of the disease.

As used herein, a "CYP2E1 inhibitor" is any compound, substance or material that can inhibit CYP2E1 activity. A number of assays are available for analysis of the CYP2E1 activity such as a human or rat liver microsome assay.

As used herein, a subject in need of the treatment according to the invention includes human and non-human mammals. Non-human mammals include, but are not limited to, companion animals such as cats, dogs and the like and farm animals such as cattle, horses, sheep, goats, swine and the like.

The term "effective amount" or the like refers to that amount of an active agent sufficient to achieve a desired therapeutic, prophylactic, and/or biological effect in a subject, such as reducing drug-induced side effects, or prohibiting, improving, alleviating, reducing or preventing one or more symptoms or conditions or progression of a disease. The actual effective amount may change depending on various reasons, such as administration route and frequency, body weight and species of the individual receiving said pharmaceutical, and purpose of administration. Persons skilled in the art may determine the dosage in each case based on the disclosure herein, established methods, and their own experience.

The term "a standard dose" as used herein refers to an effective dose of a therapeutic agent that is recommended by authoritative sources in the pharmaceutical community including the Food and Drug Administration and often used in routine practice. The term "a reduced dose" as used herein refers to a dose that is lower than a standard dose but still retains substantially the same therapeutic effects of the same therapeutic agent. Specifically, according to the invention, a reduced dose of a therapeutic drug is about 90% or less, 80% or less, 70% or less, 60% or less, 50% or less, of standard therapeutic dose of the therapeutic drug.

In some embodiments, an effective amount of active ingredients as used herein may be formulated with a pharmaceutically acceptable carrier into a pharmaceutical composition of an appropriate form for the purpose of delivery and absorption.

As used herein, "pharmaceutically acceptable" means that the carrier is compatible with the active ingredient in the composition, and preferably can stabilize said active ingredient and is safe to the individual receiving the treatment. Said carrier may be a diluent, vehicle, excipient, or matrix to the active ingredient. The composition may additionally comprise lubricants; wetting agents; emulsifying and suspending agents; preservatives; sweeteners; and flavoring agents. The composition of the present invention can provide the effect of rapid, continued, or delayed release of the active ingredient after administration to the patient.

According to the present invention, the form of said composition may be tablets, pills, powder, lozenges, packets, troches, elixers, suspensions, lotions, solutions, syrups, soft and hard gelatin capsules, suppositories, sterilized injection fluid, and packaged powder.

The composition of the present invention may be delivered via any physiologically acceptable route, such as oral, parenteral (such as intramuscular, intravenous, subcutaneous, and intraperitoneal), transdermal, suppository, and intranasal methods. Regarding parenteral administration, it is preferably used in the form of a sterile water solution, which may comprise other substances, such as salts or glucose sufficient to make the solution isotonic to blood. Preparation of an appropriate parenteral composition under sterile conditions may be accomplished with standard pharmacological techniques well known to persons skilled in the art, and no extra creative labor is required.

In certain embodiments, the compound of Formula (I) of the present invention or a pharmaceutically acceptable salt thereof can be used in preventing or treating injuries in organs e.g. in liver or kidney, which may be caused by overdose of therapeutic drugs (e.g. acetaminophen) or exposure of alcohol, a chemical agent, a biomolecule or any substance that may cause toxic effects in these organs.

Specifically, injuries in liver may include injuries, damages or loss of hepatic cells or tissues, leading to abnormal liver functions or contents of liver proteins. In some embodiments, the liver injuries as described herein are acute liver injuries which mean liver injuries of relatively rapid onset e.g. less than 12 week, particularly less than 6 weeks duration from time of onset of symptoms. In some embodiments, patients with acute liver injuries are with no background of chronic hepatic diseases.

Specifically, injuries in kidney may include injuries, damages or loss of renal cells or tissues, leading to abnormal renal functions. Such renal injuries may be identified, for example, by a decrease in glomerular filtration rate, a reduction in urine output, an increase in serum creatinine, an increase in serum cystatin C, etc. In some embodiments, the renal injuries as described herein are acute renal injuries, which may mean an abrupt or rapid decline in renal filtration function, for example, within 14 days, preferably within 7 days, more preferably within 72 hours, and still more preferably within 48 hours.

In one particular embodiment, the compound of Formula (I) of the present invention or a pharmaceutically acceptable salt thereof is capable of preventing or treating an undesired condition caused by NAPQI (N-acetyl-p-benzoquinone imine).

Therefore, the present invention provides use of the compound of Formula (I) of the present invention or a pharmaceutically acceptable salt thereof for manufacturing a medicament for preventing or treating an undesired condition caused by NAPQI (N-acetyl-p-benzoquinone imine) in a subject. The present invention also provides a method for preventing or treating an undesired condition caused by NAPQI (N-acetyl-p-benzoquinone imine) in a subject in need, comprising administering to the subject the compound of Formula (I) of the present invention or a pharmaceutically acceptable salt thereof in an amount effective to prevent or treat the undesired condition.

III. Combined Use of Compound of the Present Invention with Other Active Agent

The compound of the present invention and/or its metabolites can be administered in combination with one or more additional active agents, particularly those acting as P450 inhibitors and/or providing anti-hepatotoxicity activities and/or those with anti-fatty liver activities, so as to provide a synergistic effect, for example.

Some active agents acting as P450 inhibitors (named "a first active agent(s)") are described in PCT/CN2013/087049 (U.S. Ser. No. 14/441,317, the content of which is hereby incorporated by reference in its entirety). Particular examples of such P450 inhibitors include but are not limited to polyethylene glycol sorbitan monolaurate (Tween 20), microcrystalline cellulose, dicalcium phosphate dihydrate, Brij 35, saccharin, mannitol, Cremophor RH40, sucralose, crospovidone, sodium starch glycolate, Eudragit S100, croscarmellose sodium, Pluronic F68, menthol, low-substituted hydroxypropyl cellulose, pregelatinized starch, Dextrates NF hydrated, citric acid, Cremophor EL, Aerosol 200, Myrj 52, sorbic acid, lemon oil, hydroxypropyl cellulose, Sorbitol, acesulfame potassium, hydroxypropyl methylcellulose, lactose monohydrate, maltodextrin, Brij 58, Brij 76, Tween 80, Tween 40, PEG 400, PEG 4000, PEG 8000, Span 60, sodium benzoate, hydroxy ethylmethylcellulose, methylcellulose, Span 80, sodium cyclamate, glyceryl behenate, oxide red, glycerin monostearate, Copovidone K28, starch acetate, magnesium stearate, sodium lauryl sulfate, Providone K30, PEG 2000, and N-acetylcysteine (NAC) and any combination thereof.

In certain embodiments, the one or more first active agents to be used in combination with the compound of Formula (I) of the present invention are selected from the group consisting of dicalcium phosphate dehydrate, menthol, mannitol, sucralose, N-acetylcysteine (NAC) and any combination thereof.

Some active agents with anti-fatty liver activities (named "a second active agent") are described in PCT/CN2016/078039, the content of which is hereby incorporated by reference in its entirety. Particular examples of active agents with anti-fatty liver activities include but are not limited (ii) a second active agent selected from the group consisting of: sodium lauryl sulfate, menthol, sucralose, mannitol, sorbitol, saccharin, glycerin, sodium benzoate, oxide red, pregelatinized starch, sodium cyclamate, sorbic acid, lemon oil, citric acid, butylated hydroxyanisole, poncirin, isovitexin, eriodictyol, ergosterol, ß-myrcene, hyperoside, (+)-catechin, galangin, morin, sciadopitysin, didymin, gossypin, luteolin-7-glucoside, (+)-taxifolin, trans-cinnamic acid, diosmin, linarin, xylitol, luteolin, swertiamarin, puerarin, phloridzin, sinensetin, (−)-epigallocatechin, kaempferol, ursolic acid, silymarin, (+)-limonene, hesperidin, (−)-epicatechin-3-gallate, silybin, formononetin, myristic acid ethyl ester, eicosapentaenoic acid (EPA), wongonin, povidone K-30, protocatechuic acid, umbelliferone, hesperitin, nordihydroguaiaretic acid, neohesperidin, naringin, (−)-epicatechin, glycyrrhizin, baicalin, quercitrin, baicalein and any combinations thereof.

In certain embodiments, the one or more second active agents to be used in combination with the compound of Formula (I) of the present invention are selected from the group consisting of sodium lauryl sulfate, menthol, sucralose, mannitol, sorbitol, saccharin, glycerin, sodium benzoate, oxide red, pregelatinized starch, sodium cyclamate, sorbic acid, lemon oil, citric acid, butylated hydroxyanisole, poncirin, isovitexin, eriodictyol, ergosterol, ß-myrcene, hyperoside, (+)-catechin, galangin, morin, sciadopitysin, didymin, gossypin, luteolin-7-glucoside, (+)-taxifolin, trans-cinnamic acid, diosmin, linarin, xylitol, luteolin, swertiamarin, and any combinations thereof.

In certain embodiments, the one or more second active agents to be used in combination with the compound of Formula (I) of the present invention are selected from the group consisting of puerarin, phloridzin, sinensetin, (−)-epigallocatechin, kaempferol, ursolic acid, silymarin, (+)-limonene, hesperidin, (−)-epicatechin-3-gallate, silybin, formononetin, myristic acid ethyl ester, eicosapentaenoic acid (EPA), wongonin, povidone K-30, protocatechuic acid, umbelliferone, hesperitin, nordihydroguaiaretic acid, neohesperidin, naringin, (−)-epicatechin, glycyrrhizin, baicalin, quercitrin, baicalein and any combinations thereof In certain embodiments, the one or more second active agents to be used in combination with the compound of Formula (I) of the present invention are selected from the group consisting of eriodictyol, mannitol, menthol, sucralose, saccharin, and any combinations thereof.

In certain embodiments, the one or more second active agents to be used in combination with the compound of Formula (I) of the present invention are selected from the group consisting of (1) a combination of saccharin and mannitol, (2) a combination of menthol and mannitol, (3) a combination of sucralose and mannitol, (4) a combination of eriodictyol and mannitol, (5) a combination of eriodictyol and sucralose, (6) a combination of menthol, mannitol, and eriodictyol, and (7) a combination of sucralose, mannitol, and eriodictyol.

Specifically, the compound of Formula (I) or a pharmaceutically acceptable salt thereof and the one or more additional agents can be administered simultaneously or sequentially.

In the present invention, it is further provided that the compound of Formula (I) of the present invention or a pharmaceutically acceptable salt thereof is capable of preventing or treating an undesired condition caused by NAPQI (N-acetyl-p-benzoquinone imine).

As a particular embodiments, the present invention provides a combination of the compound of Formula (I) and/or its metabolites with N-acetylcysteine (NAC). The prevent invention also provides a method for administering N-acetylcysteine (NAC) in a subject in need, comprising administering to the subject NAC in combination with the compound of Formula (I) and/or its metabolites. In one embodiment, the combination or the method of the present invention is effective in preventing or treating a disease or disorder for which NAC is effective. In some embodiments, the disease or disorder to be treated or prevented by NAC is selected from the group consisting of Myoclonus Epilepsy, acute respiratory distress syndrome, heavy metal poisoning, influenza infection, heart disease, Sjogren's syndrome, chronic bronchitis, epilepsy (Unverricht-Lundborg type) and HIV infection.

The present invention is further illustrated by the following examples, which are provided for the purpose of demonstration rather than limitation.

EXAMPLES

Example 1: Synthesis of Compound of Formula 1 (Compound F) of the Present Invention Synthetization of ((2R,3R,4R,5R,6R)-6-(((2R,5R)-2,5-bis(chloromethyl)-3,4-dihydroxytetrahydro furan-2-yl)oxy)-3-chloro-4,5-dihydroxytetrahydro-2H-pyran-2-yl)methyl ((2R,3R,4R)-2,3,4,5,6-pentahydroxyhexyl) adipate (Formula 1) (Compound F)

The synthetic strategy for the synthesis of Formula 1 (Compound F) is shown in Scheme 1.

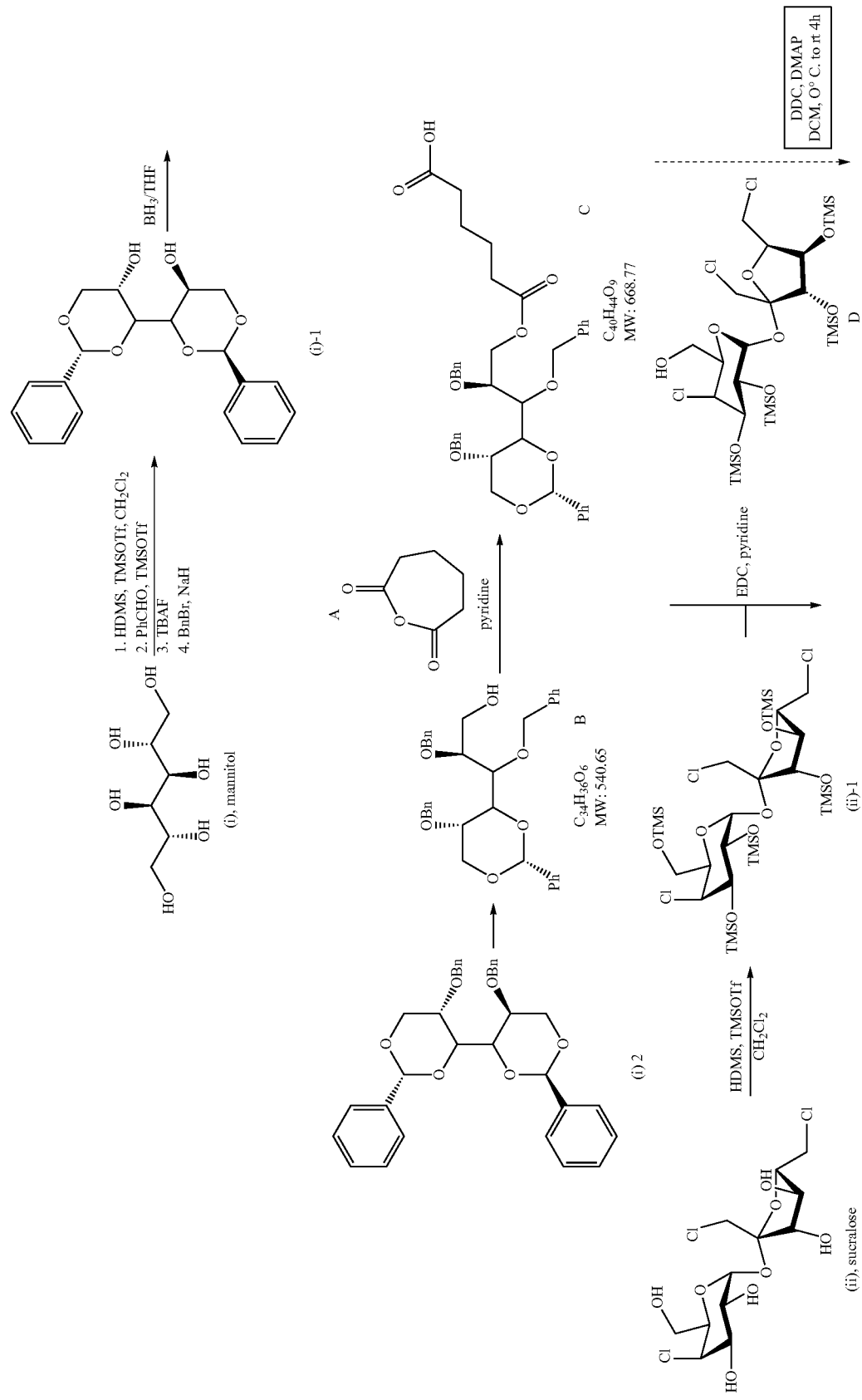
Scheme 1

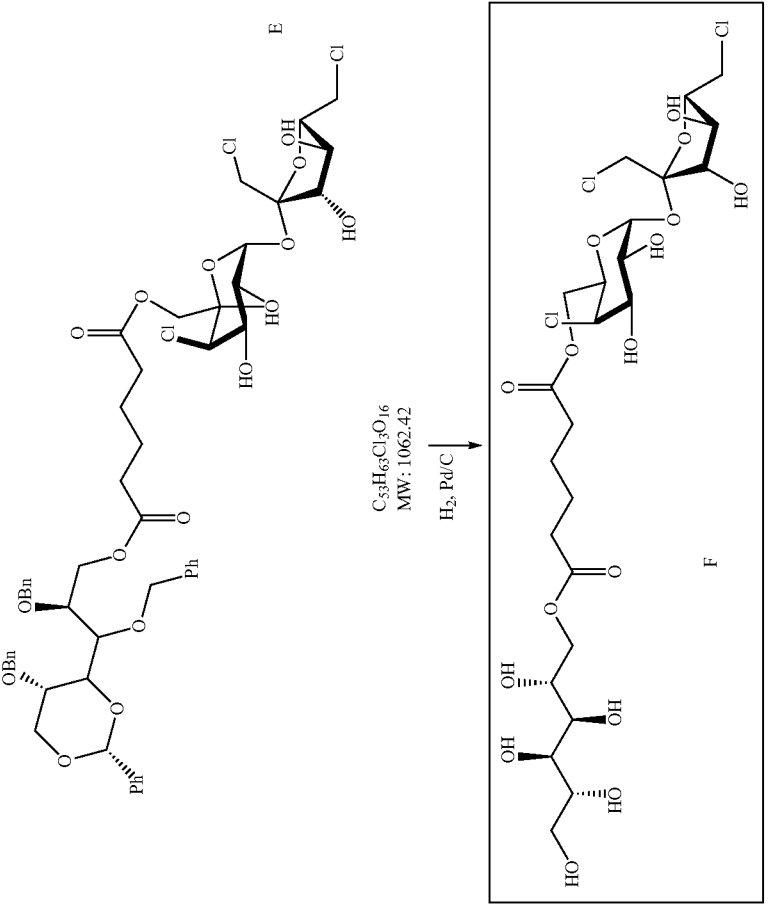
HDMS = hexamethyldisilazane
TMSOTf = Trimethylsilyl trifluoromethanesulfonate
TBAF = tetrabutylammonium fluoride
THF = tetrahydrofuran
TMS = trimethylsilyl
DCC = dicyclohexylcarbodiimid
DMAP = 4-Dimethylaminopyridine
DCM = dichloromethane
DMF = N,N′-dimethylformamide
DIBAL = diisobutylaluminum
Bn = Benzyl ether

General Methods

All chemicals were obtained from commercial sources and used as received unless otherwise stated.

The chromatographic purity of products was assessed in a condition as follows:

Mobile phase composition A: Methanol:$H_2O$=5/95 (v/v), Contain 0.05% $NH_4OH$

B: Methanol:$H_2O$=95/5 (v/v), Contain 0.05% $NH_4OH$

Chromatography system:

| Time | Pump B Conc |
|---|---|
| 0 | 15 |
| 1 | 15 |
| 5 | 80 |
| 5.1 | 15 |
| 10 | 15 |

Column type Waters® Acquity UPLO $HSST_3$, 1.8 μm, 100×2.1 mm

| Autosampler temperature | 4° C. |
|---|---|
| Column oven temperature | 45° C. |
| Flow rate | 0.35 mL/min |
| Analysis time | 10 min |
| Injection volume | 5 μL |
| Retention time | 4.8 min |

The MS analysis was conducted in a condition as follows:

| Mass spectrometer settings: | |
|---|---|
| Mass spectrometer | Triple Quadrupole MS (API Qtrap5500) Applied Biosystem, Inc. |
| Detection | MRM negative mode |
| Pro-drug: | m/z 688.9 → m/z 180.9 |

Bruker AMX-500 NMR spectrometer in MeOH-$d_4$ ($\delta_H$ 3.30, $\delta_C$ 49.0) or $CDCl_3$ ($\delta_H$ 7.24, $\delta_C$ 77.0) using Bruker's standard pulse program; in the HMQC and HMBC experiments, Δ=1 s and J=140, 8 Hz, respectively, the correlation maps consisted of 512×1 K data points per spectrum, each composed of 16 to 64 transients.

1.1 Mannitol (Compound (i)) to Compound (B)

1.1.1 Mannitol (Compound (i)) to Compound (i)-1

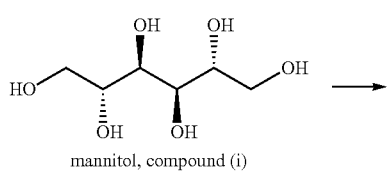

mannitol, compound (i)

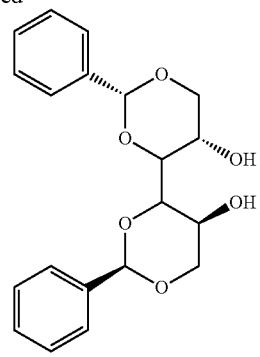

compound (i)-1

To a solution of D-mannitol (25 g, 0.137 mol) in DMF (250 mL) was added benzaldehyde (30 mL, 0.345 mmol) at r.t. under Ar. To the mixture was added concentrated sulfuric acid (10 mL) dropwise at 0° C. After being allowed to warm up gradually to the r.t., the mixture was stirred for 3 day. Then the mixture was poured into ice water (250 mL) and n-hexane (200 mL) under vigorous stirring. After the mixture was warm up to r.t., the precipitate was filtered and washed with n-hexane. The precipitate was suspended in chloroform and heated under reflux for 15 min under vigorous stirring. When the mixture reached r.t., the undissolved precipitate was collected and Recrystallization from EtOH gave desired product as white solid (9.86 g, 20%). $R_f$=0.45 (EA/Hex=1/1).

1.1.2 Compound (i)-1 to Compound (i)-2

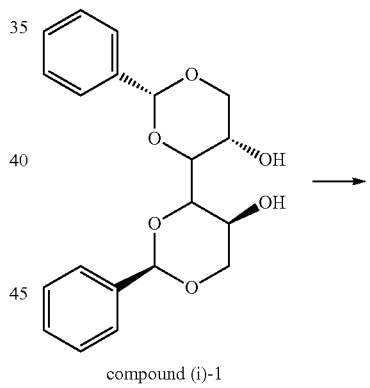

compound (i)-1

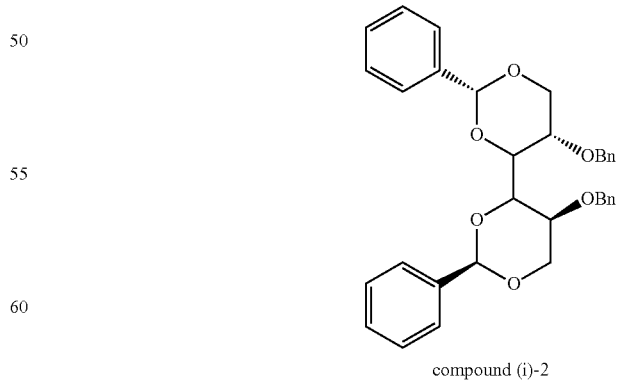

compound (i)-2

To a solution of 1,3,4,6-dibenzylidene (10 g, 27.9 mmol) in DMF (100 mL) was added benzyl bromide (7.96 mL, 66.96 mmol) at r.t. under Ar. The mixture was cooled to 0°

C. then 60% NaH (2.68 g, 66.96 mmol) was added in few time. After being allowed to warm up gradually to the r.t., the mixture was stirred for overnight. Then the reaction was quenched by water (dropwise) and extracted with NaHCO₃ (aq) and dichloromethane. The organic layer was dried with MgSO₄, concentrated in vacuum. The residue was purified by column chromatography on silica gel to afford desired product. (10.39 g, 69%). $R_f$=0.2 (EA/Hex=1/6).

1.1.3 Compound (i)-2 to Compound (B)

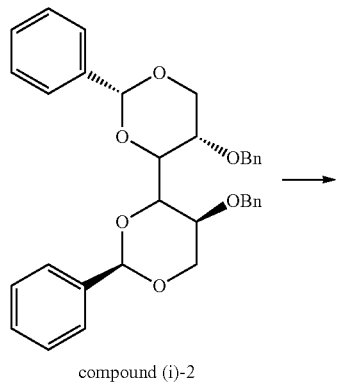

compound (i)-2

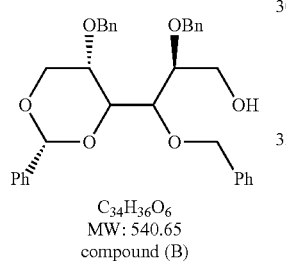

$C_{34}H_{36}O_6$
MW: 540.65
compound (B)

To a solution of 2,5-dibenzyl-1,3,4,6-dibenzylidene (1.5 g, 2.78 mmol) in toluene (12.5 mL) was cooled to −18° C. (ice-salt bath). 1.2 M DIBAL was added (18.5 mL, 22.3 mmol) dropwise and warmed to r.t. After 1.5 h, the reaction was cooled to 0° C. then quenched by MeOH and 15% KOH(aq). The mixture was extracted with DCM, organic layer was dry with MgSO₄ and concentrated in vacuum. The residue was purify by column chromatography on silica gel to afford desired product. (709 mg, 47%). R$=0.1 (EA/HEX=1/5).

1.2 Sucralose (Compound (ii)) to Compound (D)

1.2.1 Compound (ii) to Compound (ii)-1

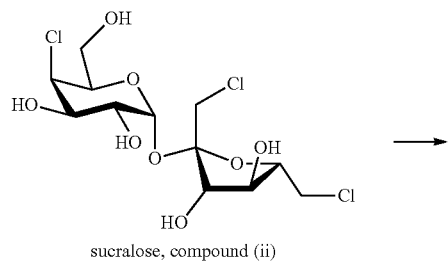

sucralose, compound (ii)

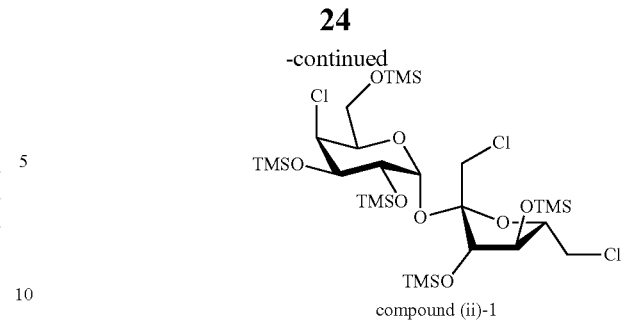

compound (ii)-1

To a solution of sucralose (1 g, 2.5 mmol) in DCM (10 mL) was added HMDS (2.6 mL, 12.57 mmol) and TMSOTf (45 μL, 0.25 mmol). The reaction was stirred for overnight in r.t. The reaction was concentrated in vacuum and pass through the cotton, wash by hexane. The filtrate was concentrated again in vacuum to get the product in quant. (1.9 g, quant.). $R_f$=0.9 (EA/HEX=1/8).

1.2.2 Compound (ii)-1 to Compound (D)

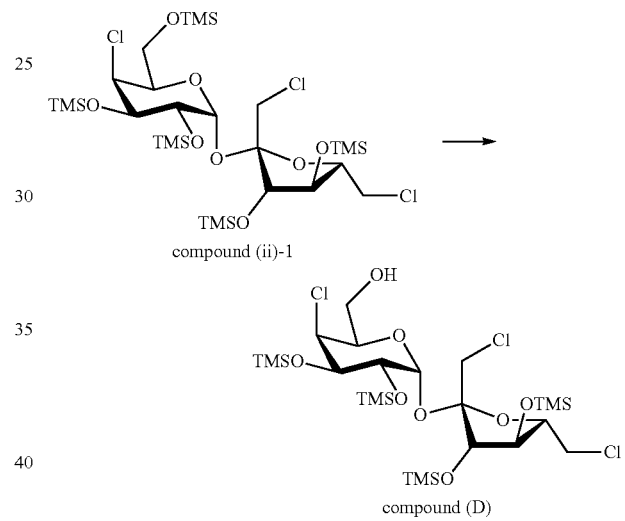

To a solution of penta-TMS sucralose (5 g, 6.6 mmol) in pyridine (150 mL) was added 0.1 M pyridine-TsCl solution (6.6 mL) and stirred for 3 days with open flask. The reaction was concentrate in vacuum and purified by column chromatography on silica gel to afford desired product. (1.4 g 30%). R/=0.5 (EA/HEX=1/8).

1.3 Synthesis of 6-oxo-6-((2R,3R,4R)-2,3,4-tris(benzyloxy)-4-(2-phenyl-1,3-dioxolan-4-yl)butoxy)hexanoic acid (Compound (C))

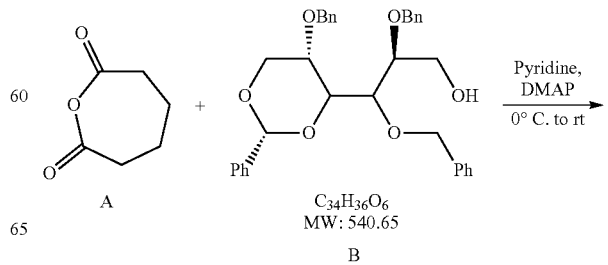

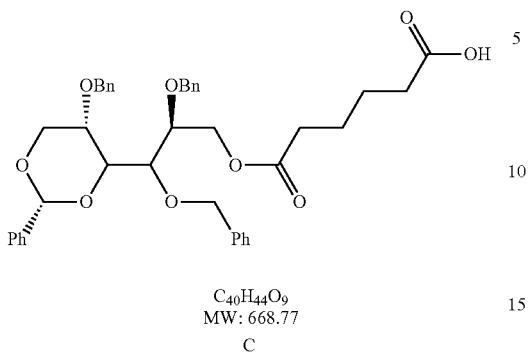

C₄₀H₄₄O₉
MW: 668.77

C

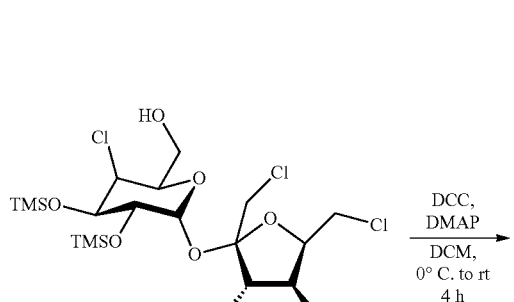

D

In a flame dry R.B. flask compound A (165 mg, 1 eq.) was dissolved in DCM (5 mL) at 0° C., then to this was added pyridine (0.2 mL) and DMAP (50 mg). Reaction mixture was then stirred for 10 min, followed by Comp. B (59 mg, 1.5 eq.) was added. Reaction mixture was then stirred at room temperature for 5 h. TLC confirmed the completion of reaction. Reaction mixture was evaporated to dryness of rotavapour under reduced pressure. The crude compound was further purified by column chromatography to afford the desired compound as a colorless oil (136 mg, 67%).

1.4 Synthesis of ((2R,3S,4R,5R,6R)-6-(((2R,5R)-2,5-bis(chloromethyl)-3,4-bis((trimethylsilyl)oxy)tetrahydrofuran-2-yl)oxy)-3-chloro-4,5-bis((trimethylsilyl)oxy)tetrahydro-2H-pyran-2-yl)methyl ((2R,3R,4R)-2,3,4-tris(benzyloxy)-4-(2-phenyl-1,3-dioxolan-4-yl)butyl) adipate

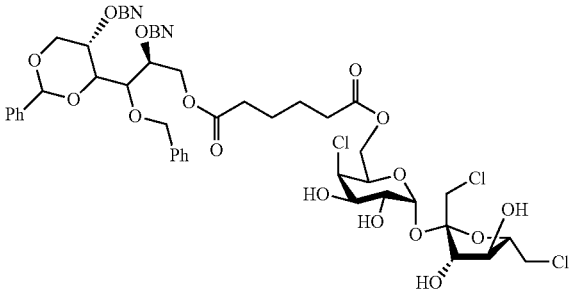

C₅₃H₆₃Cl₃O₁₆
MW: 1062.42

E

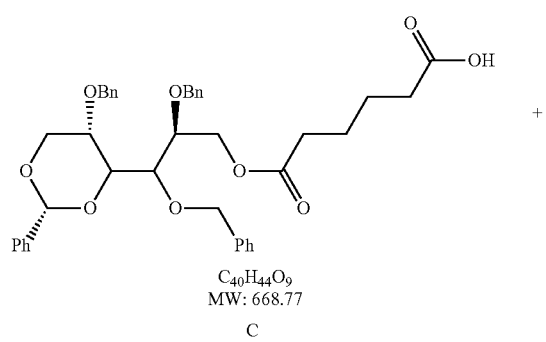

C₄₀H₄₄O₉
MW: 668.77

C

To ice cold solution of compound C (100 mg, 1.0 eq.) in DCM was added DCC (35 mg, 1.15 eq.) and stirred for 10 min. Then to this Compound D (112 mg, 1.2 eq.) and DMAP (5 mg, 0.25 eq. catalytic) was added. Reaction mixture was allowed to warm to rt and stirred for 4 hours. TLC confirmed the completion of reaction. Reaction mixture was evaporated to dryness on rotavapour under reduced pressure. The crude compound was then purified by column chromatography using neutral silica gel and 5 to 15% ethyl acetate in Hexane with 1% Triethyl amine as an eluent to afford desired compound E as a colourless oil (84 mg, 42%).

1.5 Synthesis of (((2R,3R,4R,5R,6R)-6-(((2R,5R)-2, 5-bis(chloromethyl)-3,4-dihydroxytetrahydro furan-2-yl)oxy)-3-chloro-4,5-dihydroxytetrahydro-2H-pyran-2-yl)methyl ((2R,3R,4R)-2,3,4,5,6-pentahydroxyhexyl) adipate (Compound F)

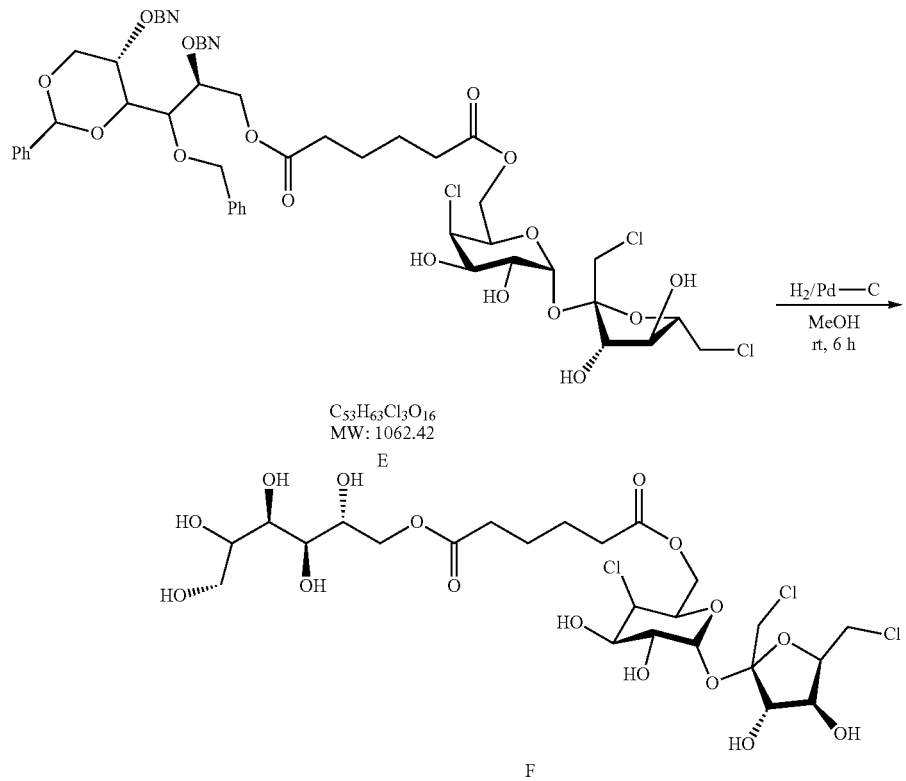

In a flame dry Single neck R.B. flask compound E (500 mg, 1 eq.) was dissolved in dry MeOH (20 mL), solution was then degassed by nitrogen gas (Nitrogen gas syringe was deep inside the solution and Nitrogen was purge for 15 min.). Then 10% Pd—C(200 mg, 33% w/w) was added cautiously to reaction mixture. Finally, reaction mixture was stirred under hydrogen balloon pressure for 6 hours. TLC confirmed the completion of reaction. Reaction mixture was then filtered through celite bed and the bed was washed with dry methanol. The filtrate was evaporated to dryness of rotavapour under reduced pressure. Final compound was then kept under high vacuum to afford desired final compound F as colorless semisolid or white solid (190 mg, 73%). The structure of compound F were identified by high-resolution mass spectrophotometry and $^{13}C$ NMR.

Example 2: Compound F as a Prodrug, Generating Metabolites when Incubated with Blood (In Vitro)

2.1 Materials and Methods

Fresh human whole-blood were used for drug hydrolysis studies. Drug (10 mg, compound F) was dissolved in 1 mL solution (20% methanol). Drug hydrolysis (n=3) was performed in 20 mL of fresh whole-blood aliquots containing 1.0 mg of drug in a 50-mL flask thermostat at 37° C. in a shaking water bath. At time 0, the drug was added, and after various times of incubation, the blood samples were collected at 0.25, 0.5, 0.33, 0.75, 1, 2, 4, 6, 12 and 24 hrs. Blood sample were used 1 mL acetonitrile to quench the enzymatic hydrolysis of the drug as samples were obtained. Pro-drug and its related metabolites, such as C6-mannitol, mannitol and sucralose in blood were determined by An API QTrap5500 triple-quadrupole mass spectrometer equipped with an ion-spray (ESI) source. The ESI interface was used in the negative-ion mode.

2.2 Results

The pro-drug was monitored at a transition of m/z 688.9→180.9, Sucralose was monitored at a transition of m/z 395→359; mannitol was monitored at a transition of m/z 452.3→273.3; C6-mannitol was monitored at a transition of m/z 309→101.1. All the compounds were identified by high-resolution mass spectrophotometry and $^{13}C$ NMR. The structure of C6-mannitol (formula (2)) is as follows:

(2)

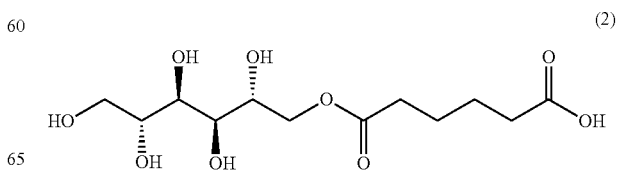

The hydrolysis of pro-drug in blood was expressed by plotting the percentage of Pro-drug remaining and the percentage of sucralose, mannitol and C6-mannitol increasing versus time after incubation of the pro-drug in blood (FIG. 1). The results shows that compound F acts as a pro-drug which turns into its metabolites including sucralose, mannitol and C6-mannitol after incubated with blood in vitro.

Example 3: Pharmacokinetics Study in SD (Sprague Dawley)-Rats (In Vivo)

3.1 Materials and Methods

SD-rats were orally administered pro-drug at a dose of 3.67 mg/kg BW. Blood samples were collected into heparinized micro centrifuge tubes at intervals of 0, 0.5, 1, 2, 4, 6, 8, 12, and 24 h. Plasma samples were immediately obtained by centrifuging the blood samples at 8,000 rpm for 10 min. The plasma samples were then stored at −80° C. until use. The plasma samples were analyzed for pro-drug and its related metabolites, such as mannitol and sucralose by API QTrap5500 triple-quadrupole mass spectrometer equipped with an ion-spray (ESI) source. The ESI interface was used in the negative-ion mode.

3.2 Results

The pro-drug was monitored at a transition of m/z 688.9→180.9, Sucralose was monitored at a transition of m/z. 395→359; mannitol was monitored at a transition of m/z 452.3→273.3; C6-mannitol was monitored at a transition of m/z 309→101.1.

Figure 2:
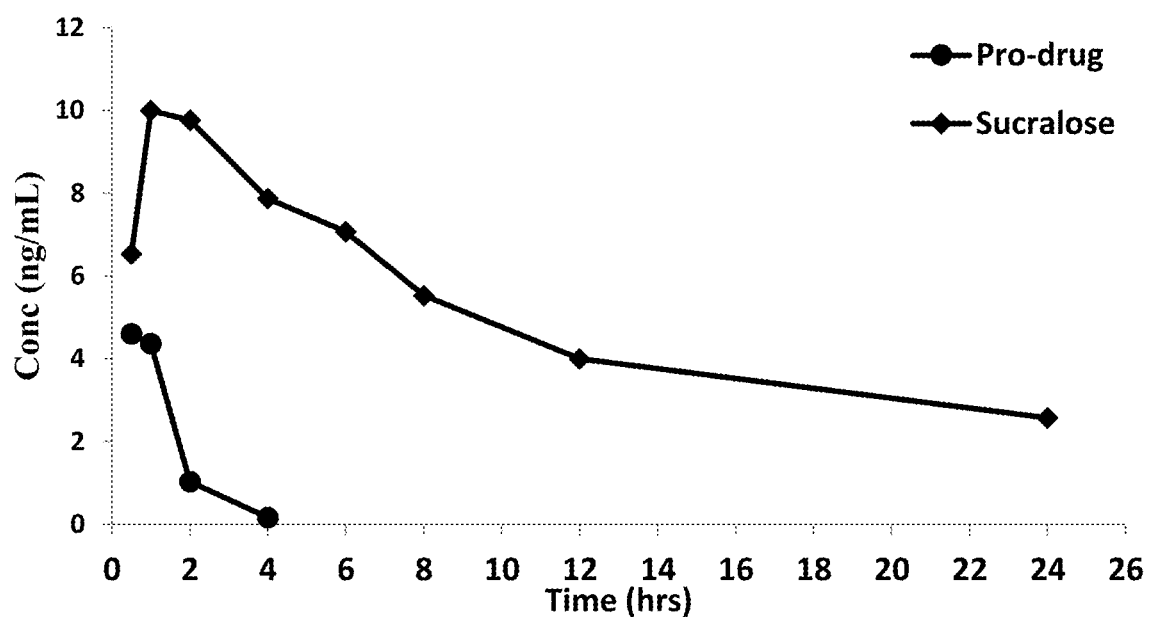
FIG. 2 shows the plasma concentration vs. time profile for pro-drug and sucralose after oral administration of pro-drug in SD-rats.
Figure 3:
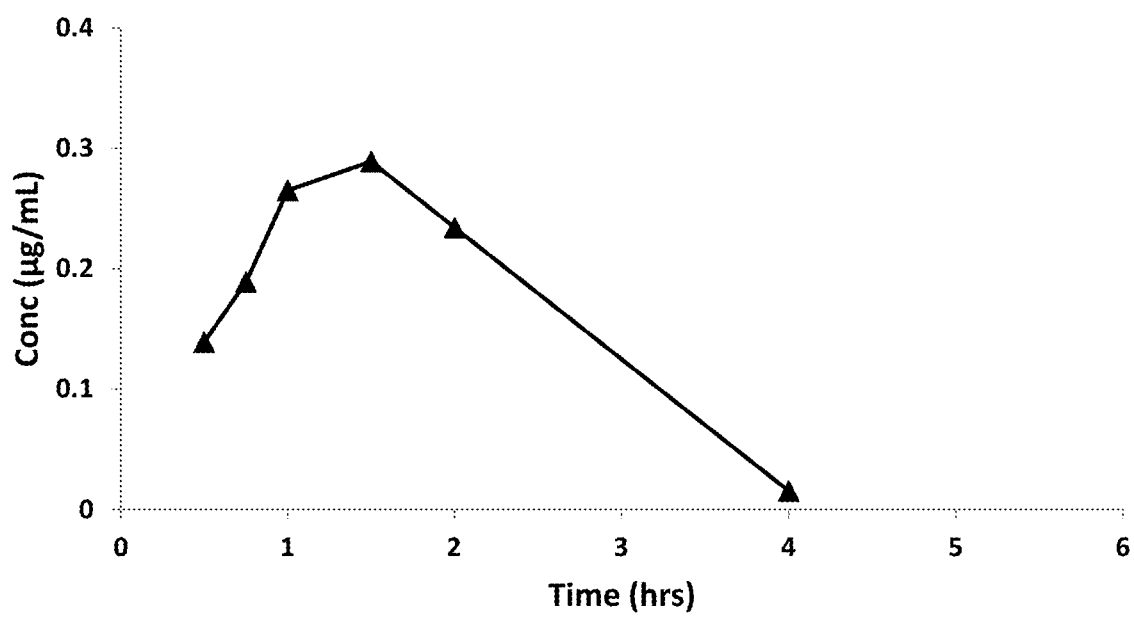
FIG. 3 shows the plasma concentration vs. time profile for mannitol after oral administration of pro-drug in SD-rats.

FIG. 2 and FIG. 3 shows the plasma concentration time curves of pro-drug and its related metabolites, such as sucralose and mannitol in SD-rats with single oral dosing of 3.67 mg/kg pro-drug, respectively. The results shows that compound F acts as a pro-drug which converts into its metabolites including sucralose, mannitol and C6-mannitol after administration in animals in vivo

Example 4: CYP2E1 Inhibitory Activity Assays

4.1 Materials and Methods

This example is preparation of microsomes from human liver for in vitro screening of CYP450 isozyme inhibitors. Effective human hepatic CYP450 isozyme inhibitors were tested and the principle for testing the CYP450 isozyme inhibitors is based on the reaction of microsomal CYP450 isozyme prepared from the liver of different origin and its specific substrate Chlorzoxazone (CZX). After addition of the test sample, the amount of CYP450 isozyme metabolite standard 6-OH-CZX (6-Hydroxy-Chlorzoxazone) is specific used for calculation of the CYP450 isozyme (CYP2E1) inhibition ratio of the test sample by using the amount of 6-OH-CZX of the control group as the baseline.

All samples were tested in triplicate. To determine the percentage inhibition, each test compound was dissolved in 1, 2, 4 µg/mL, to three different concentrations. The CYP2E1 activity levels in the presence of the test compounds were compared with the control incubations. The 500-µL reaction mixture, containing 0.5 mg of microsomal protein, was incubated with 320 µM CZX in the presence of 5 mM $MgCl_2$ and 1 mM NADPH in 50 mM phosphate buffer with pH 7.4 at 37° C. for 30 min. The reaction was terminated by ice-cold acetonitrile, and then 4-hydroxyl tolbutamide was added as an internal standard. The organic phase was evaporated to dryness and reconstituted into the mobile phase (methanol:water=1:1) prior to liquid chromatography-tandem mass spectrometry (LC-MS/MS) analysis. An API 3000 triple-quadrupole mass spectrometer equipped with an ion-spray (ESI) source was used to determine 6-OH-CZX in the human liver microsomes. The ESI interface was used in the positive-ion mode. The 6-OH-CZX was monitored at a transition of m/z 284.5→185.9. Analysis of the results: convert the detected signal values obtained from LC/MS/MS into the amount (pmol) of CYP450 isozyme metabolite standard 6-Hydroxy-Chlorzoxazone using the control group as the baseline, i.e. the CYP450 isozyme inhibition ratio of the control group is 0%. The CYP450 isozyme activity levels in the presence of the test compounds were compared with the control incubations.

4.2 Results

Diethyldithiocarbamic acid (DDTC) is a well-known inhibitor of CYP2E1. At a concentration of 100 µM, DDTC treatment resulted in 90.9% inhibition of CYP2E1 in human liver microsomes (measured using CZX as a CYP2E1 substrate). On the basis of the observed inhibitory activity of DDTC, we tested the new compound (pro-drug) and its related metabolites for CYP2E1 inhibition at concentrations of 4, 2 and 1 µg/mL. The results as summarized in Table 1.

TABLE 1

The inhibition ratios of CYP2E1 inhibitors from in-vitro screening of human liver microsomes

| Test concentration | Test compound CYP 2E1 inhibition ratio (%) | | |
|---|---|---|---|
| | 4 µg/mL | 2 µg/mL | 1 µg/mL |
| Control group | 0 | 0 | 0 |
| Positive control (DDTC) | (100 µM) | (50 µM) | (10 µM) |
| | 90.9 ± 0.8 | 51.2 ± 3.2 | 11.2 ± 2.4 |
| Pro-drug | 45.7 ± 2.5 | 33.3 ± 4.1 | 17.7 ± 0.7 |
| Metabloite_1 (mannitol) | 40.3 ± 1.6 | 34.1 ± 4.1 | 30.1 ± 2.4 |
| Metabolite_2 (sucralose) | 32.9 ± 4.6 | 30.2 ± 2.8 | 25.1 ± 1.4 |
| Intermediate metabolite (C6-mannitol with protecting groups, Formula C) | 70.3 ± 2.8 | 56.5 ± 1.7 | 40.5 ± 2.3 |

The CYP 2E1 inhibition ratios of the test compound detected in the human liver microsomes are shown in Table 1. From the results, test compounds, including the pro-drug (compound F) and its metabolites i.e. mannitol, sucralose and C6-mannitol with protecting group (Formula C), have been demonstrated to be effective as P450 2E1 inhibitors, among which 4 µg/mL intermediate metabolite of pro-drug (i.e. C6-mannitol with protecting groups, Formula C) showed the best inhibition effect (70.3±2.8%).

Example 5: Assays of Liver Injuries Induced by Acetaminophen (APAP) and $CCl_4$

5.1 Materials and Methods 5.1.1 Reagents

All organic solvents are HPLC grade and are purchased from Tedia (Fairfield, OH, USA). APAP is purchased from Sigma (St. Louis, MO USA), galactose injectable solution is manufactured by Southern Photochemical Co. and is prepared by dissolving 400 g of galactose (Sigma) in 1 L of buffer solution containing isotonic salts for injections.

5.1.2 Animals

Male SD (Sprague-Dawley) rats weighing 175-280 g were purchased from the National Laboratory Animal Center (NLAC), Taiwan. The study was conducted in accordance with the Guidelines for Conducting Animal Studies of the National Health Research Institute and all rats were placed in the air/humidity controlled environment under the 12 hours of day/12 hours of night cycle and with unlimited water and food supply. During the course of the study, the weights of rats were monitored continuously with normal water supply.

5.1.3 Treatments

5.1.3.1 Liver Injuries Induced by APAP

Mannitol and sucralose were used to perform the animal test (rat) in view of liver injuries induced by APAP.

In the normal control (Group 1), animals were not fed with APAP. In the control group of APAP-induced liver injuries (Group 2), animals were fed with a single dose of APAP in the amount of 2,000 mg per kilogram of body weight to induce hepatotoxicity. In the positive control group of treatment with NAC (Group 3), animals were fed with a single dose of APAP in the amount of 2,000 mg per kilogram of body weight to induce hepatotoxicity, and 4 hours later, a 24-hour treatment period by tube feeding was started, including first administration of 140 mg of NAC (per kilogram of body weight) and later administration of 70 mg of NAC (per kilogram of body weight) every 4 hours for five times. In the experimental group (Group 4), animals were fed with a single dose of APAP in the amount of 2,000 mg per kilogram of body weight to induce hepatotoxicity, and 4 hours later, a 24-hour treatment period by tube feeding was started, including six dosing with the ingredients of the present invention every 4 hours, as follows:

(a) (Group 4.1): administration of mannitol at a dose less than or equivalent to 100 mg per person every 4 hours for 24 hours, (b) (Group 4.2): administration of double dose of mannitol as in Group 4.1 every 4 hours for 24 hours, (c) (Group 4.3): administration of sucralose at a dose less than or equivalent to 100 mg per person every 4 hours for 24 hours, (d) (Group 4.4): administration of double dose of sucralose of Group 4.3 every 4 hours for 24 hours, (e) (Group 4.5): administration of a combination of 0.5 times the dose of mannitol as in Group 4.1 and 0.5 times the dose of sucralose as in Group 4 . . . 3 per kilogram of body weight every 4 hours for 24 hours, (f) (Group 4.6): administration of a combination of the dose of mannitol as in Group 4.1 and the dose of sucralose as in Group 4.3 every 4 hours for 24 hours, (g) (Group 4.7): administration of a combination of 1.5 times the dose of mannitol as in Group 4.1 and 1.5 times the dose of sucralose as in Group 4.3 every 4 hours for 24 hours, (h) (Group 4.8): administration of a combination of double dose of mannitol as in Group 4.1 and double dose of sucralose as in Group 4.3 every 4 hours for 24 hours, and (i) (Group 4.9): first administration of 140 mg of NAC per kilogram of body weight and later administration of a combination of 70 mg of NAC plus double dose of mannitol as in Group 4.1 and double dose of sucralose as in Group 4.3 every 4 hours for five times.

After the 24-hour treatment period, blood was collected from the tail artery of the rats for AST/SLT assays. Subsequently, rats were subjected to GSP tests. Finally, rats were sacrificed and histological analysis was performed.

5.1.3.2 Liver Injuries Induced by $CCl_4$

Mannitol and sucralose were chosen from the active ingredients as described herein to perform the animal test (mice) in view of liver injuries induced by $CCl_4$.

In the normal control, animals were administered with normal saline by intraperitoneal injection. In the control group of $CCl_4$ induced liver injuries, animals were intraperitoneally injected with 10 ml/kg $CCl_4$ (40% in corn oil) to induce hepatotoxicity. In the experimental group, animals were intraperitoneally injected with 10 ml/kg $CCl_4$ (40% in corn oil) to induce hepatotoxicity, and 4 hours later, different ingredients of the present invention were administered by tube feeding. Blood was collected from the mice before administration with the ingredients of the present invention or at 24 hours after administration with the ingredients of the present invention for AST/ALT assays. Finally, animals were sacrificed at day 2 and blood were collected for AST/ALT assay and histological analysis was performed.

On the other hand, other experimental groups of mice were fed with the ingredients of the present invention for 12 weeks and the mice were subjected to GSP tests.

5.1.4 Blood Samples

After completion of the treatments, rats were sacrificed under ether anesthesia, and blood was collected from the tail artery of the rats and placed in a test tube containing EDTA. The plasma was centrifuged at 13,000 at 4° C. for 15 minutes and the isolated plasma was transferred to Eppendorf tubes in aliquots and stored at −80° C.

5.1.5 Biochemical Analysis

Liver damage is quantified by measuring plasma AST and ALT activity. AST and ALT are common indicators of hepatotoxicity and are measured by using the Synchron LXi 725 system (Beckman Instruments, U.S.).

5.1.6 Optic Microscope

Following scarification of the rats, histological analysis was performed. Liver samples were fixed with 10% phosphate-buffered formalin, dehydrated an embedded in paraffin, Sections were prepared in 5 μm thickness and then stained with hematoxylin and eosin and subjected to Periodic acid Schiff stain (PAS). The stained sections were observed under the optic microscope.

5.1.7 Quantitative Tests of Liver Function

After the study was completed, all rats were subjected to GSP test. Rats were i.v. injected with 0.4 g/ml BW galactose solution 0.5 g/kg within 30 seconds and one blood sample was collected at 5, 10, 15, 30, 45 and 60 minutes post injection from the tail vein. Colorimetric galactose dehydrogenase is used to quantify the concentration of galactose and the test concentration ranges from 50 to 1,000 μg/ml. The within-day variation of each concentration is calculated using standard deviation and coefficient of variation (CV) and the maximum allowable coefficient of variation is 10% CV, whereas day-to-day variation is examined by comparing the slope and intercept of calibration curves. The GSP is the blood galactose concentration obtained 60 seconds after stopping the 30-second injection.

5.1.8 Statistical Analysis

All data are represented in mean±standard deviation (SD) and the results are calculated using ANOVA to determine the significance. Statistical Package of the Social Science program (Version 13, SPSS Inc.) is used for calculations followed by post hoc test to examine the least significant difference for multiple comparisons so as to confirm the significant differences between groups and the average difference between groups was significant $p<0.05$.

5.2 Results

5.2.1 Mannitol and Sucralose and Other Ingredients are Effective in Treating Liver Injuries Induced by APAP The results are shown in Table 2.

TABLE 2

| Liver function parameters | GSP (mg/L) | AST (IU/L) | ALT (IU/L) | Total HAI score | Survival (Day 14, n/n) |
|---|---|---|---|---|---|
| Group 1: Normal control (NC, n = 6) | 220 ± 24 | 186 ± 16 | 65 ± 16 | 0.0 ± 0.0 | 3/3 |
| Group 2: APAP control (2,000 mg/kg, n = 12) | 1017 ± 170 | 1151 ± 310 | 746 ± 143 | 8.6 ± 0.5 | 2/12 |
| Group 3: NAC (140 mg/kg of NAC followed by 5 × 70 mg/kg NAC at 4 h intervals, n = 6) | 393 ± 68*** | 428 ± 74*** | 221 ± 69*** | 4.2 ± 0.8*** | 3/6 |
| Group 4.1 (n = 3) (Mannitol at a dose less than or equivalent to 100 mg per person) × 6 | 565 ± 177*** | 455 ± 78*** | 209 ± 16*** | 4.0 ± 0.0*** | 1/3 |
| Group 4.2 (n = 3) (Double dose of Group 4.1 (mannitol)) × 6 | 354 ± 56*** | 300 ± 40*** | 166 ± 15*** | 4.0 ± 1.0*** | 3/3 |
| Group 4.3 (n = 3) (Sucralose at a dose less than or equivalent to 100 mg per person) × 6 | 332 ± 42*** | 331 ± 41*** | 154 ± 49*** | 4.0 ± 1.0*** | 3/3 |
| Group 4.4 (n = 3) (Double dose of Group 4.3 (sucralose)) × 6 | 309 ± 54*** | 277 ± 78*** | 136 ± 48*** | 3.0 ± 1.0*** | 3/3 |
| Group 4.5 (n = 3) (0.5 times the dose of Group 4.1 (mannitol) + 0.5 times the dose of Group 4.3 (sucralose)) × 6 | 332 ± 61*** | 360 ± 81*** | 149 ± 19*** | 2.0 ± 1.0*** | 3/3 |
| Group 4.6 (n = 3) (the dose of Group 4.1 (mannitol) + the dose of Group 4.3 (sucralose)) × 6 | 271 ± 52*** | 193 ± 34*** | 81 ± 18*** | 1.5 ± 1.0*** | 6/6 |
| Group 4.7 (n= 3) (1.5 times the dose of Group 4.1 (mannitol) + 1.5 times the dose of Group 4.3 (sucralose)) × 6 | 265 ± 53*** | 203 ± 24*** | 83 ± 25*** | 1.0 ± 1.0*** | 3/3 |
| Group 4.8 (n = 3) (double dose of Group 4.1 (mannitol) + double dose of Group 4.3 (sucralose)) × 6 | 227 ± 25*** | 159 ± 21*** | 69 ± 10*** | 0.5 ± 0.5*** | 6/6 |
| Group 4.9 (n = 3) 140 mg/kg NAC + 5 × (70 mg NAC + double dose of Group 4.1 (mannitol + double dose of Group 4.3 (sucralose)) | 233 ± 41*** | 171 ± 25*** | 58 ± 9*** | 0.3 ± 0.5*** | 6/6 |
| Group 5 (n = 6) (Aerosil 200 at a dose less than or equivalent to 100 mg per person) | 280 ± 98*** | 247 ± 43*** | 66 ± 18*** | 2.8 ± 1.0*** | 6/6 |
| Group 6 (n = 6) (Sodium starch glycolate at a dose less than or equivalent to 100 mg per person) | 294 ± 30*** | 248 ± 37*** | 81 ± 27*** | 2.7 ± 1.2*** | 6/6 |
| Group 7 (n = 6) (Crospovidone at a dose less than or equivalent to 100 mg per person) | 372 ± 90*** | 323 ± 40*** | 175 ± 61*** | 2.8 ± 1.5*** | 6/6 |
| Group 8 (n = 6) (Microcrystalline cellulose at a dose less than or equivalent to 100 mg per person) | 259 ± 36*** | 217 ± 28*** | 72 ± 21*** | 2.2 ± 1.0*** | 6/6 |

TABLE 2-continued

| Liver function parameters | GSP (mg/L) | AST (IU/L) | ALT (IU/L) | Total HAI score | Survival (Day 14, n/n) |
|---|---|---|---|---|---|
| Group 9 (n = 6) (Povidone K-30 at a dose less than or equivalent to 100 mg per person) | 287 ± 38*** | 220 ± 53*** | 71 ± 26*** | 2.5 ± 1.0*** | 6/6 |

*p < 0.05,
**p < 0.01,
***p < 0.005: comparison of the experimental groups with APAP control The results show that liver injuries has occurred in the APAP hepatotoxicity group. In contrast, such liver injuries and survival rate can be improved by use of mannitol and/or sucralose, in a dose dependent manner. Especially, a combination of mannitol and sucralose achieves a synergistic effect; the results are similar to those of normal control and even better than the positive control of standard treatment with NAC. In addition, other ingredients including Aerosil 200, Sodium starch glycolate, Crospovidone, Microcrystalline cellulose and Povidone K-30 are found effective in treating the liver injuries, also better than the positive control of standard treatment with NAC.

The improved results are also reflected in the corresponding liver tissues.

Figure 4:
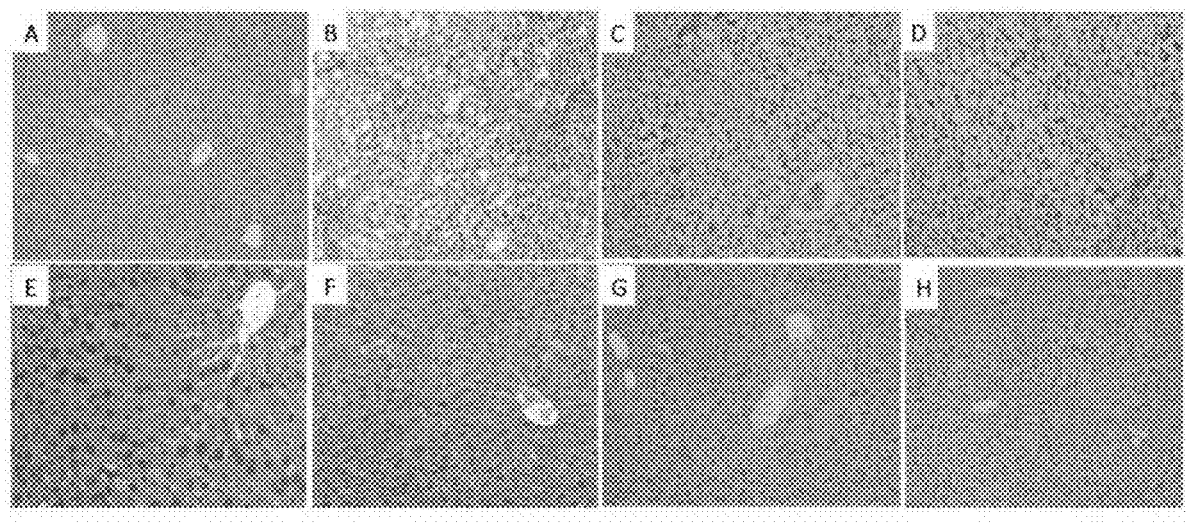
FIG. 4 shows the H&E staining results of liver tissues in animals. (A) the normal control, (B) the control group of APAP-induced liver injuries, (C) the positive control group of treatment with NAC, (D) the experimental group of treatment with mannitol (1.67 mg/kg), (E) the experimental group of treatment with sucralose (1.67 mg/kg), (F) the experimental group of treatment with mannitol (2.51 mg/kg) plus sucralose (2.51 mg/kg), (G) the experimental group of treatment with mannitol (3.34 mg/kg) plus sucralose (3.34 mg/kg), and (H) the experimental group of treatment with NAC and a combination of mannitol (3.34 mg/kg) and sucralose (3.34 mg/kg).

FIG. 4 shows the results of the histological analysis. The liver tissue sections from the rats in the APAP hepatotoxicity group showed that hepatocytes surrounding the central vein are broken with visible vacuolization and reduced number of nucleuses, some hepatocytes even showed the signs of necrosis and liver damage is more severe when compared with the hepatocytes from rats in the normal control group (FIG. 4B). On the contrary, liver structure of rats in the control group are normal, the hepatocytes are intact and arranged in order with no vacuolization (FIG. 4A). As for the liver sections from the experimental groups with treatment by mannitol and/or sucralose, the hepatocytes are relatively intact with visible nucleus and less vacuolization (FIG. 4D, E, F, G, H). Especially, a combination of mannitol and sucralose achieves the best protective effect (FIG. 4G); the results are even better than the positive control of standard treatment with NAC (FIG. 4C).

5.2.2 Mannitol is Effective in Treating Liver Injuries Induced by CCL

The results are shown in Table 3.

TABLE 3

| | Liver function parameters | | | |
|---|---|---|---|---|
| Groups | GSP (mg/L) | AST (IU/L) | ALT (IU/L) | Total HAI score |
| Normal control (n = 10) | 315 ± 48 | 88 ± 20 | 57 ± 17 | 0.0 ± 0.0 |
| $CCl_4$ control group (n = 10) | 914 ± 205*** | 815 ± 216*** | 770 ± 274*** | 6.2 ± 2.1*** |
| Dose of kaempfrol less than or equivalent to 100 mg per person (n = 10) | 456 ± 101*** | 198 ± 105*** | 128 ± 40*** | 4.3 ± 13* |
| Dose of epigallocetechin-3-gallate less than or equivalent to 100 mg per person (n = 10) | 312 ± 140*** | 144 ± 49*** | 95 ± 36*** | 1.7 ± 0.9*** |
| Dose of quercetin less than or equivalent to 100 mg per person (n = 10) | 286 ± 70*** | 115 ± 40*** | 93 ± 26*** | 1.1 ± 0.7*** |
| Dose of mannitol less than or equivalent to 100 mg per person (n = 10) | 290 ± 78*** | 91 ± 28*** | 77 ± 22*** | 0.8 ± 0.5*** |

Statistic analysis: Anova and LSD tests.
***p < 0.005,
**p < 0.01,
*p < 0.05, comparison of the experimental groups with $CCl_4$ control group.

The results show that liver injuries has occurred in the $CCl_4$ control group. In contrast, such liver injuries can be improved by use of mannitol.

Example 6: Assays of Fatty Liver 6.1 Materials and Methods 6.1.1 Cell Lines and Cell Culture Media The activity of the various ingredients as described herein, including mannitol and sucralose and others, in reduction of fat content was analyzed by using human hepatoma cell line Hep G2.

Dulbecco's Modified Eagle's Medium (DMEM) was used to prepare DMEM culture Nos. A-F listed in Table 4 for carrying out subsequent experiments.

TABLE 4

Preparations of DMEM culture media Nos. A-F

| DMEM cultures | Preparation methods |
| --- | --- |
| No. A | DMEM was dissolved in 1,400 mL of water with stirring, and then 2 g of 4-(2-hydroxyethyl)-1-piperazine-ethanesulfonic acid (HEPES) was added to form a solution, to which a sodium bicarbonate solution (4 g of sodium bicarbonate powder dissolved in 400 mL of water by stirring) was added, and the volume was made up to 2,000 mL with water. The pH of the resulting solution was adjusted to 7.3 ± 0.05 by adding 5N HCl. After being filtered through a 0.2 μm sterile membrane, the final solution was dispensed into sterile serum vials and stored at 4° C. |
| No. B | 50 mL of deactivated fetal bovine serum (FBS), 5 mL of sodium pyruvate (100 mM), 5 mL of penicillin (100 U/mL) and streptomycin (100 U/mL), and 5 mL of MEM non-essential amino acid solution(100X) were added into 450 mL of DMEM culture No. A. |
| No. C | 5 mL of sodium pyruvate (100 mM), 5 mL of penicillin (100 U/mL) and streptomycin (100 U/mL), and 5 mL of MEM non-essential amino acid solution(100X) were added into 450 mL of DMEM culture No. A. |
| No. D | DMEM culture No. B was added into the oleate/albumin complex. The oleate/albumin complex was prepared according to the method presented by Van Harken et al. in 1969 (J Biol Chem. 1969 May 10; 244(9): 2278-85). The method included taking 25 mL of DMEM culture No. A, into which 5 g of bovine serum albumin (BSA) was added, and then 5N sodium hydroxide solution was added to adjust the pH to 7.4 to form a mixture. The mixture was then placed in an ice bath at 0° C. to form the BSA solution. The oleic acid was dissolved in 50 ml of alcohol (95%) and then titrated to the phenolphthalein titration endpoint with 1N sodium hydroxide solution. The alcohol was blown away by flowing helium. The resulting sodium oleate was dissolved in DMEM culture No. A at 37° C. to form a sodium oleate solution. At last, the BSA solution was added dropwise into the sodium oleate solution with stirring to form the oleate/albumin complex solution. |
| No. E | Various amounts silymarin were dissolved in DMEM culture No. C. |
| No. F | Various amounts of the test compounds of the present invention were dissolved in DMEM culture No. C. |

The DMEM cultures Nos. A-F were preserved at 2-8° C., and warmed up in a water bath at 37° C. before the experiments.

6.1.2 Cell Counts and Survivability Test

Dead cells would take up 0.4% trypan blue and then had a color; whereas live cells exclude certain dyes due to the intact cell membranes and had a clear color. 100 μl of cell suspension and equal volume of 0.4% trypan blue were mixed uniformly to form a mixture. Some of the mixture (about 20 μl) was added into the groove above the chamber of the hemocytometer, which was then covered with a cover slip for observing under the optical microscope. Live cells were not stained, and dead cells were blue.

6.1.3 Oleic Acid-Induced Formation of Fatty Liver Cells from HepG2 Cell Lines

HepG2 cell lines (15×10$^6$ cells) were cultured in DMEM culture No. B, incubated in an incubator with 5% $CO_2$ at 37° C. for 24 hours, cultured in DMEM culture No. C (serum-free medium) for 24 hours, and finally cultured in DMEM culture No. D (containing oleate/albumin complex) for another 48 hours to induce HepG2 cell lines to form fatty liver cells.

6.1.4 Treatments for Each Group of Fatty Liver Cells

HepG2 cell lines were divided into six groups, including: (1) Blank: no treatment; (2) DMSO group: cells from Blank were treated with dimethyl sulfoxide (DMSO); (3) Control: induction with oleic acid to form fatty liver cells; (4) Vehicle group: fatty liver cells formed by induction with oleic acid were treated with DMSO; (5) Positive control: fatty liver cells were treated with silymarin; and (6) Test Group: fatty liver cells were treated with various compounds of the present invention.

6.1.5 Determination of Triglyceride (TG) in Cells

After incubation for 72 hours, the treated cells from each group were successively washed twice in PBS, and then incubated with 0.5 ml of trypsin/EDTA for 3 minutes. Afterwards, the cells were scraped with 2 ml of PBS and then transferred to the centrifuge tube to be shattered by ultrasonic. A volume of 20 μl cell extracts was taken to determine the content of protein. TG determination was performed using commercially available combination of agents (Randox). The TG content obtained above was divided by the protein content to get a ratio, which represented the relative content of TG in cells.

6.1.6 Animals for Experiments

B6 mice recommended in the specification "Method for evaluating the liver protection and health care efficacies of health food" announced by the Department of Health of Taiwan were chosen for animal testing. More than four mice were used in each group of the pre-test, while more than twelve mice were used in each group of the confirmatory test. Male mice bred at 23±2° C. in an animal room with 55±15% relative humidity under normal light/dark cycle (7:00 AM-7:00 PM lights on/7:00 PM-7:00 AM lights off) and weighing 18-23 g were purchased from BioLASCO (Taipei) and housed at Laboratory Animal Center in National Defense Medical Center. The animal test was carried out according to the guideline for animal experiment of National Health Research Institutes. Mice were fed with normal feed at 3-5 g/day and unlimited supply of water for 1-2 weeks and investigated for health condition. The weight of mice was recorded once a week.

6.1.7 Animal Grouping

The tested animals were grouped randomly into Blank, High Fat Diet control (HFD), Positive Control (PS), and Test group. The animals of Blank were fed with normal feed. The animals of HFD were fed with high fat feed. The animals of PS were fed with high fat feed, and additionally fed with silymarin (5 mg/kg/day) by a tube. The animals of Test group were fed with high fat feed, and additionally fed with test compounds by a tube.

6.1.8 Test Methods

The animals of Blank were fed casually with normal feed for 12 weeks, while the animals of HFD, PS, and Test group were fed casually with high fat feed for 12 weeks. After 8 weeks of feeding, the animals of Blank and HFD were fed with deionized water by a tube once a day; the animals of PS were fed with silymarin by a tube once a day; and the animals of Test Group were fed with test compounds by a tube once a day for a duration of 4 or 8 weeks.

Before testing and in the eighth, twelfth, and sixteenth week after testing, blood was collected from the cheek or the heart. At the end of testing, all mice were weighted and then sacrificed, and blood was collected from the cheek or the heart simultaneously. The blood specimens of mice rested at room temperature for one hour to clot, and then the serum was separated by centrifugation in a refrigeration centrifuge at 15,700×g at 4° C. for 5 minutes. Afterwards, biochemical indices of liver function, including aspartate transaminase (AST), alanine aminotransferase (ALT), triglyceride (TG), total cholesterol (TCHO/TC), low-density lipoprotein cholesterol (LDL-C), and high-density lipoprotein cholesterol (HDL-C), were detected by the automatic blood biochemistry analyzer.

In addition, abdominal fat and liver specimens were taken from the abdomens of sacrificed mice and weighted to compare the weight of fat and liver and obtain the ratio of liver weight to body weight. Two tissue blocks with a volume of approximately 1 cm$^3$ were cut from the largest right lobe of liver, fixed in 10% neutral formalin solution, and then embedded with paraffin for sectioning. The cut sections proceeded with H&E staining for histopathological observation. Moreover, the rest of the liver was frozen for preservation and detection of the contents of triglyceride and total cholesterol in the liver. Furthermore, the liver function of animals of each group were analyzed by Galactose Single Point Method, which was recognized and recommended for quantification of remaining liver function in clinical use by U.S. FDA and Ministry of Health and Welfare, Taiwan. At the end of the tests, 0.5 g of galactose (G.S.P.® 0.4 g/mL) per kg of animal was administered via intravenous. One hour after the administration, about 0.5 ml of whole blood was taken by using a filter paper to evaluate liver function of mice. The higher the value of GSP was, the worse the remaining liver function would be. (FDA: "Guidance for Industry: Pharmacokinetics in Patients with Impaired. Hepatic Function-Study Design, Data Analysis and Impact on Dosing and. Labeling. 2003.

6.1.9 Histopathological Tissue Sectioning:

At the end of the test, all mice were sacrificed. One tissue block with a volume of approximately 1 cm$^3$ was cut from the largest right lobe of liver, fixed in 10% neutral formalin, and then dehydrated and hyalinized in various concentrations of ethanol (30, 50, 70, 95. 99.5%) and xylene. Afterwards, xylene was replaced with hot paraffin solution. At last, the tissue was embedded with paraffin solution. The finished paraffin specimen was cut into 5 μm-thickness paraffin sections by the microtome. The sections were pasted on clean slides, dried at 37° C., and then stained by H&E staining.

6.1.10 Hematoxylin and Eosin Staining (H&E)

Liver tissue sections were deparaffinized in xylene for 30 minutes, and then successively rehydrated twice in 99.5%, 95%, 70%, 50%, and 30% aqueous ethanol for 30 minutes respectively. After being soaked in distilled water for 10 minutes, the sections could be stained. The sections were first immersed in hematoxylin for 30 seconds to stain cell nuclei, then washed with distilled water for a few minutes, stained with eosin for 2-5 minutes, and washed with distilled water for a few minutes again. After staining process was finished, the sections were dehydrated successively in 50%, 70%, 95%, and 100% aqueous ethanol twice for 30 seconds respectively, hyalinized twice in xylene, and finally sealed and stored with mounting media.

6.1.11 Histopathological Observation

In order to observe the changes of lesion, fat accumulation, necrosis, or fibrosis in liver cells when there was an ongoing liver damage, liver tissues were H&E stained to evaluate the degree of liver fat accumulation. All the histopathological sections were cut from the same position on the largest right lobe of liver for eliminating bias in subjective observation, and then subject to pathological staining. As for the assessment of semi-quantitative analysis in pathology, it had to be confirmed by a physician or a veterinary pathologist who conducted a double-blind analysis to score (NAS score) and compare all the sections without knowing the test design. At last, the differential analysis of each group was performed by statistical methods.

6.1.12 Analysis of Liver Antioxidant Capacity

About 0.1 g of liver tissue was taken from the sacrificed animal and homogenized by centrifuge with a biomasher for 10 minutes. A 9-fold weight (w/w) of buffer (pH 7.4, 50 mmol/L Tris-HCl, 180 mmol/L KCl) was added to the homogenized tissue, which was then mixed well by a Vortex mixer for use. The resulting homogenization solution samples of liver tissue was used to analyze the various members of liver antioxidant systems, including glutathione peroxidase (GPx), glutathione (GSH), glutathione reductase (Grd), and superoxide dismutase (SOD). Methods of related analysis can be found in the known literatures, for example, the draft of "Method for evaluating the liver protection and health care efficacies of health food" announced by the Ministry of Health and Welfare, Taiwan.

6.1.13 Statistical Analysis

All data were expressed as means±standard deviation (SD). Statistically significant difference of the test results was determined by calculation of one-way ANOVA using Statistical Package of the Social Science program, Version 13, SPSS Inc. Thereafter, multiple comparisons were carried out by using least significant difference method in post hoc test to confirm the significant difference between groups. The average difference between groups is judged to be significant when $p<0.05$.

6.2 Results 6.2.1 Cell Experiments

In cell experiments, the results of TG content reduction in HepG2 cells determined in Positive Control (silymarin) were listed in Table 5.

TABLE 5

Efficacy of silymarin in reduction of TG content in HepG2 fat cells of Positive Control

| Silymarin concentration (μM) | TG content in cells (μg/mg protein) | Reduction rate of TG (%) |
|---|---|---|
| 0 (Control) | 59.43 ± 4.60 | — |
| 1.0 | 44.17 ± 2.41 | 29 ± 8 |
| 5.0 | 44.59 ± 11.53 | 28 ± 10 |
| 1.0 | 26.38 ± 9.12 | 63 ± 11 |
| 100 | 20.48 ± 4.76 | 78 ± 5 |

The results of TG content reduction in HepG2 fat cells determined using constant concentration of test compounds were shown in Table 6. It can be seen from the results that the test compounds exhibited different degrees of TG content reduction effects in fatty liver cells formed from induced HepG2 cells under the condition of constant test concentration, as compared with Control. The equation for calculating reduction rate (%) of TG was as follows: [1−(TG content of Test Group−TG content of Blank)/(TG content of Oleic acid induction Group−TG content of Blank)]×100%.

TABLE 6

TG content in fatty liver cells reduced by test compounds

| Tested substances (1.0 μM) | TG reduction rate (%) |
|---|---|
| Silymarin Control | 35.33 ± 1.96 |
| Puerarin | 49.91 ± 7.73 |
| Phloridzin | 42.35 ± 6.05 |
| Daidzein | 42.3 ± 5.34 |
| Sodium lauryl sulfate | 38.73 ± 4.65 |
| Poncirin | 38.12 ± 7.22 |
| Sinensetin | 36.97 ± 4.84 |
| (−)-Epigallocatechin | 36.78 ± 6.67 |
| Kaempferol | 36.51 ± 4.78 |
| Isovitexin | 35.93 ± 3.35 |
| Ursolic Acid | 35.86 ± 8.92 |
| Eriodictyol | 35.11 ± 0.87 |
| (+)-Limonene | 35.02 ± 10.04 |
| Hesperidin | 34.81 ± 5.25 |
| Ergosterol | 34.19 ± 3.69 |
| β-myrcene | 33.97 ± 11.22 |
| (−)-Epicatechin-3-gallate | 32.7 ± 4.33 |
| Hyperoside | 30.51 ± 2.8 |
| Silybin | 30.26 ± 3.24 |
| (+)-Catechin | 29.57 ± 4.02 |
| Formononetin | 29.55 ± 1.44 |
| Myristic acid ethyl ester | 28.88 ± 3.91 |
| Galangin | 28.11 ± 8.62 |
| Suralose | 26.68 ± 2.93 |
| Eicosapentaenoic acid (EPA) | 26.15 ± 6.14 |
| Morin | 25.84 ± 10.65 |
| Mannitol | 22.35 ± 5.74 |
| Sciadopitysin | 21.83 ± 5.04 |
| Wongonin | 20.78 ± 1.12 |
| Didymin | 20.37 ± 12.69 |
| Gossypin | 20.25 ± 4.63 |
| Sorbitol | 20.06 ± 2.57 |
| Luteolin-7-glucoside | 19.33 ± 4.59 |
| Povidone K-30 | 18.93 ± 5.13 |
| Protocatechuic acid | 18.57 ± 7.6 |
| (+)-Taxifolin | 17.91 ± 8.35 |
| Saccharin | 17.53 ± 6.96 |
| Umbelliferone | 17.4 ± 2.57 |
| Glycerin | 16.23 ± 4.25 |
| Hesperitin | 16.08 ± 5.55 |
| Nordihydroguaiaretic acid | 15.92 ± 2.3 |
| Trans-Cinnamic Acid | 15.85 ± 0.82 |
| Sodium benzoate | 14.35 ± 4.86 |
| Oxide red | 13.59 ± 2.08 |
| Neohesperidin | 13.29 ± 7.21 |
| Naringin | 12.69 ± 3.72 |
| Diosmin | 11.86 ± 3.73 |

TABLE 6-continued

TG content in fatty liver cells reduced by test compounds

| Tested substances (1.0 μM) | TG reduction rate (%) |
|---|---|
| (−)-Epicatechin | 10.76 ± 8.92 |
| Glycyrrhizin | 10.55 ± 7.4 |
| Linarin | 9.24 ± 12.34 |
| Baicalin | 9.21 ± 6.21 |
| Quercitrin | 9.15 ± 9.24 |
| Xylitol | 7.36 ± 6.34 |
| Baicalein | 7.09 ± 10.88 |
| Luteolin | 6.95 ± 15.23 |
| Swertiamarin | 6.72 ± 11.04 |
| Butylated hydroxyanisole | 6.21 ± 3.8 |
| Sodium cyclamate | 4.77 ± 4.49 |
| Menthol | 66.24 ± 1.87 |
| Citric acid | 2.55 ± 4.43 |
| Lemon oil | 0.56 ± 1.07 |
| Pregelatinized starch | 7.18 ± 13.41 |
| Sorbic acid | 2.03 ± 1.96 |

TABLE 6-1

A portion of test compounds from Table 6 that reduced TG content in fatty liver cells

| Tested substances (1.0 uM) | TG reduction rate (%) |
|---|---|
| Puerarin | 49.91 ± 7.73 |
| Phloridzin | 42.35 ± 6.05 |
| Daidzein | 42.3 ± 5.34 |
| Sinensetin | 36.97 ± 4.84 |
| (−)-Epigallocatechin | 36.78 ± 6.67 |
| Kaempferol | 36.51 ± 4.78 |
| Ursolic Acid | 35.86 ± 8.92 |
| Silymarin of Control | 35.33 ± 1.96 |
| (+)-Limonene | 35.02 ± 10.04 |
| Hesperidin | 34.81 ± 5.25 |
| (−)-Epicatechin-3-gallate | 32.7 ± 4.33 |
| Silybin | 30.26 ± 3.24 |
| Formononetin | 29.55 ± 1.44 |
| Myristic acid ethyl ester | 28.88 ± 3.91 |
| Eicosapentaenoic acid (EPA) | 26.15 ± 6.14 |
| Wongonin | 20.78 ± 1.12 |
| Povidone K-30 | 18.93 ± 5.13 |
| Protocatechuic acid | 18.57 ± 7.6 |
| Umbelliferone | 17.4 ± 2.57 |
| Hesperitin | 16.08 ± 5.55 |
| Nordihydroguaiaretic acid | 15.92 ± 2.3 |
| Neohesperidin | 13.29 ± 7.21 |
| Naringin | 12.69 ± 3.72 |
| (−)-Epicatechin | 10.76 ± 8.92 |
| Glycyrrhizin | 10.55 ± 7.4 |
| Baicalin | 9.21 ± 6.21 |
| Quercitrin | 9.15 ± 9.24 |
| Baicalein | 7.09 ± 10.88 |

TABLE 6-2

A portion of test compounds (Bioflavonoids) from Table 6 that reduced TG content in fatty liver cells

| Tested substances (1.0 uM) | TG reduction rate (%) |
|---|---|
| Poncirin | 38.12 ± 7.22 |
| Isovitexin | 35.93 ± 3.35 |
| Eriodictyol | 35.11 ± 0.87 |
| Ergosterol | 34.19 ± 3.69 |
| β-myrcene | 33.97 ± 11.22 |
| Hyperoside | 30.51 ± 2.8 |
| (+)-Catechin | 29.57 ± 4.02 |
| Galangin | 28.11 ± 8.62 |
| Morin | 25.84 ± 10.65 |
| Sciadopitysin | 21.83 ± 5.04 |
| Didymin | 20.37 ± 12.69 |

TABLE 6-2-continued

A portion of test compounds (Bioflavonoids) from Table 6 that reduced TG content in fatty liver cells

| Tested substances (1.0 uM) | TG reduction rate (%) |
|---|---|
| Gossypin | 20.25 ± 4.63 |
| Luteolin-7-glucoside | 19.33 ± 4.59 |
| (+)-Taxifolin | 17.91 ± 8.35 |
| Trans-Cinnamic Acid | 15.85 ± 0.82 |
| Diosmin | 11.86 ± 3.73 |
| Linarin | 9.24 ± 12.34 |
| Xylitol | 7.36 ± 6.34 |
| Luteolin | 6.95 ± 15.23 |
| Swertiamarin | 6.72 ± 11.04 |

TABLE 6-3

A portion of test compounds (excipients) from Table 6 that reduced TG content in fatty liver cells

| Tested substances (1.0 uM) | TG reduction rate (%) |
|---|---|
| Sodium lauryl sulfate | 38.73 ± 4.65 |
| Sucralose | 26.68 ± 2.93 |
| Mannitol | 22.35 ± 5.74 |
| Sorbitol | 20.06 ± 2.57 |
| Saccharin | 17.53 ± 6.96 |
| Glycerin | 16.23 ± 4.25 |
| Sodium benzoate | 14.35 ± 4.86 |
| Oxide red | 13.59 ± 2.08 |
| Butylated hydroxyanisole | 6.21 ± 3.8 |
| Sodium cyclamate | 4.77 ± 4.49 |
| Menthol | 66.24 ± 1.87 |
| Citric acid | 2.55 ± 4.43 |
| Lemon oil | 0.56 ± 1.07 |
| Pregelatinized starch | 7.18 ± 13.41 |
| Sorbic acid | 2.03 ± 1.96 |

6.2.2 Animal Experiments

In the animal experiments, all the animals were treated to induce fatty liver, except the animals of Blank that were fed with normal feed. After eight weeks, the animals of each group were given different treatment for four or eight weeks in addition to the original feed. The animals of Blank and HFD were fed with deionized water; the animals of PS were fed with silymarin; and the animals of Test Group were fed with different test compounds, including puerarin, phloridzin, eriodictyol, sucralose, mannitol, saccharin, hesperitin, menthol, and combinations thereof.

6.2.2.1 The Effects on Body Weight, Liver Weight, and Weight of Body Fat of Animals and Safety Evaluation of Test Compounds From the results of animal experiments, the liver weight, weight of body fat, and increase of body weight of animals of each group were listed in Table 7-1 and 7-2.

TABLE 7-1

The analysis results of liver weight and weight of body fat due to test compounds

| Items Unit | Abdominal fat weight g | Liver weight g |
|---|---|---|
| Blank (n = 13) | 0.6 ± 0.2 *** | 1.6 ± 0.2 0.6 |
| HFD (n = 12) | 2.8 ± 0.4 | 1.6 ± 0.4 2.8 |
| Positive Control | | |
| Silymarin 5.0 mg/kg (n = 6) | 2.0 ± 0.4 *** | 1.2 ± 0.3 *** |
| Silymarin 1.5 mg/kg (n = 6) | 2.3 ± 0.5 * | 1.5 ± 0.1 |
| Single test compound | | |
| Phloridzin 2.5 mg/kg (n = 6) | 2.3 ± 0.6 * | 1.3 ± 0.1 * |
| Eriodictyol 2.5 mg/kg (n = 6) | 2.7 ± 0.6 | 1.3 ± 0.1 ** |
| Sucralose 7.5 mg/kg (n = 6) | 2.4 ± 0.3 | 1.4 ± 0.1 |
| Sucralose 1.5 mg/kg (n = 6) | 2.1 ± 0.6 ** | 1.5 ± 0.2 |
| Menthol 1.5 mg/kg (n = 6) | 2.3 ± 0.6 * | 1.6 ± 0.2 |
| Mannitol 7.5 mg/kg (n = 6) | 2.4 ± 0.3 | 1.4 ± 0.1 |
| Mannitol 4.5 mg/kg (n = 6) | 2.7 ± 0.3 | 1.4 ± 0.2 |
| Mannitol 1.5 mg/kg (n = 6) | 2.0 ± 0.3 *** | 1.4 ± 0.2 |
| Saccharin 1.5 mg/kg (n = 3) | 2.3 ± 0.5 | 1.5 ± 0.1 |
| Puerarin 2.5 mg/kg (n = 6) | 2.8 ± 0.3 | 1.4 ± 0.2 |
| Hesperitin 2.5 mg/kg (n = 6) | 3.0 ± 0.5 | 1.5 ± 0.1 |
| Combinations of two test compounds | | |
| Saccharin + Mannitol 1.5 mg/kg + 1.5 mg/kg (n = 6) | 2.7 ± 0.4 | 1.4 ± 0.2 2.7 |
| Menthol + Mannitol 4.5 mg/kg + 4.5 mg/kg (n = 6) | 3.0 ± 0.5 | 1.6 ± 0.3 3.0 |
| Menthol + Mannitol 1.5 mg/kg + 1.5 mg/kg (n = 6) | 2.3 ± 0.6 | 1.5 ± 0.3 2.3 |

TABLE 7-1-continued

The analysis results of liver weight and weight of body fat due to test compounds

| Items<br>Unit | Abdominal fat weight<br>g | Liver weight<br>g |
|---|---|---|
| Combinations of three test compounds | | |
| Menthol + Mannitol + Eriodictyol<br>.5 mg/kg + .5 mg/kg + .8 mg/kg(n = 6) | 2.6 ± 0.6 | 1.4 ± 0.2 2.6 |

Data were expressed as means ± SD.
Statistical difference resulted from ANOVA and LSD was denoted by words.
* $p < 0.05$,
** $p < 0.01$,
*** $p < 0.005$, as compared with HFD.
Hesperitin
Puerarin
Eriodictyol
Phloridzin
Mannitol
Menthol
Sucralose
Saccharin
TG: triglyceride
TC: total cholesterol

TABLE 7-2

The analysis results of increase of body weight due to test compounds

| Items<br>Unit | Increase of body weight<br>g |
|---|---|
| Blank (n = 13) | 15.6 ± 7.9 |
| HFD (n = 12) | 14.0 ± 8.4 |
| Positive Control | |
| Silymarin 5.0 mg/kg (n = 6) | 10.2 ± 12.7 |
| Silymarin 1.5 mg/kg (n = 6) | 10.9 ± 4.3 |
| Single test compound | |
| Phloridzin 2.5 mg/kg (n = 6) | 13.7 ± 10.7 |
| Eriodictyol 2.5 mg/kg (n = 6) | 8.3 ± 6.7 |
| Sucralose 7.5 mg/kg (n = 6) | 8.3 ± 5.4 |
| Sucralose 1.5 mg/kg (n = 6) | 17.0 ± 5.6 |
| Menthol 1.5 mg/kg (n = 6) | 19.6 ± 5.0 |
| Mannitol 7.5 mg/kg (n = 6) | 10.3 ± 8.5 |
| Mannitol 4.5 mg/kg (n = 6) | 11.1 ± 7.7 |
| Mannitol 1.5 mg/kg (n = 6) | 10.9 ± 7.4 |
| Saccharin 1.5 mg/kg (n = 3) | 27.7 ± 12.7 ** |
| Puerarin 2.5 mg/kg (n = 6) | 21.7 ± 3.1 * |
| Hesperitin 2.5 mg/kg (n = 6) | 14.5 ± 8.3 |
| Combinations of two test compounds | |
| Saccharin + Mannitol<br>1.5 mg/kg + 1.5 mg/kg (n = 6) | 16.6 ± 6.4 |
| Menthol + Mannitol<br>4.5 mg/kg + 4.5 mg/kg (n = 6) | 15.6 ± 5.0 |
| Menthol + Mannitol<br>1.5 mg/kg + 1.5 mg/kg (n = 6) | 14.9 ± 6.3 |
| Combinations of three test compounds | |
| Menthol + Mannitol + Eriodictyol<br>.5 mg/kg + .5 mg/kg + .8 mg/kg (n = 6) | 21.7 ± 3.9 * |

Data were expressed as means ± SD.
Statistical difference resulted from ANOVA and LSD was denoted by words.
* $p < 0.05$,
** $p < 0.01$,
*** $p < 0.005$, as compared with HFD.
Hesperitin
Puerarin
Eriodictyol
Phloridzin
Mannitol
Menthol
Sucralose
Saccharin
TG: triglyceride
TC: total cholesterol It was shown from the results that the weight of abdominal fat increased in animals induced with fatty liver. Among the test compounds administered separately, mannitol, menthol, and sucralose could reduce the weight of abdominal fat in animals significantly.

In addition, no abnormal condition was observed in animals of Test Group after the test compounds were administered. No animal died during the test. Occurrence of diseases or clinical symptoms caused by the test compounds was not observed from necropsy studies of sacrificial animals after the tests. Therefore, the test compounds were safe.

6.2.2.2 the Test Compounds are Effective in Reducing Lipid in Liver

Figure 5:
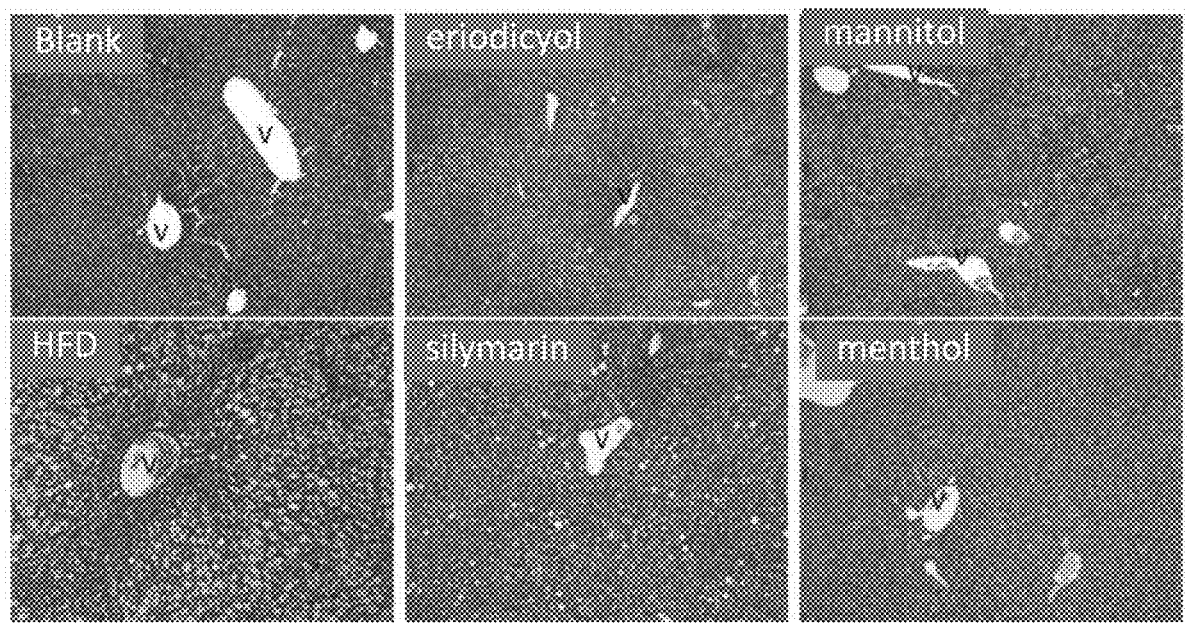
FIG. 5 shows liver tissue sections taken from mice that were induced fatty liver, and then treated with different test compounds by groups for four weeks.

FIG. 5 showed the mice that were induced to exhibit fatty liver whose liver cells near hepatic portal area (including the bile duct, portal vein, hepatic artery) were covered with many large vesicular fat droplets and hepatocellular ballooning appeared, indicating that the animal model of fatty liver was successfully established by induction.

The results of animal experiments showed that a plurality of test compounds exhibited the effects of lipid reduction in animal livers after administration for a period of 4 or 8 weeks. The results were shown in Tables 8-1 and 8-2.

TABLE 8-1

| | | |
|---|---|---|
| Test compounds could reduce liver lipids in animals (administration period of 4 weeks) | | |
| Items | TG in liver | TC in liver |
| Unit | mg/g liver | mg/g liver |
| Blank (n = 13) | 25.0 ± 9.2 *** | 2.5 ± 0.4 *** |
| HFD (n = 12) | 132.0 ± 69.2 | 6.6 ± 3.5 |
| Positive Control | | |
| Silymarin 5.0 mg/kg (n = 6) | 46.8 ± 14.4 *** | 3.0 ± 0.9 *** |
| Silymarin 1.5 mg/kg (n = 6) | 69.9 ± 32.3 ** | 3.7 ± 0.4 ** |
| Single test compound | | |
| Phloridzin 2.5 mg/kg (n = 6) | 48.9 ± 14.1 *** | 2.9 ± 0.5 *** |
| Eriodictyol 5.0 mg/kg (n = 6) | 54.2 ± 15.0 *** | 3.0 ± 0.9 *** |
| Eriodictyol 2.5 mg/kg (n = 6) | 43.1 ± 13.1 *** | 3.8 ± 1.1 ** |
| Sucralose 7.5 mg/kg (n = 6) | 56.8 ± 20.0 *** | 5.0 ± 0.9 |
| Sucralose 1.5 mg/kg (n = 6) | 68.9 ± 37.5 ** | 3.0 ± 0.9 *** |
| Menthol 1.5 mg/kg (n = 6) | 87.3 ± 72.3 * | 4.4 ± 3.5 * |
| Mannitol 7.5 mg/kg (n = 6) | 53.8 ± 24.4 *** | 4.7 ± 1.2 |
| Mannitol 4.5 mg/kg (n = 6) | 71.5 ± 45.5 *** | 7.2 ± 2.8 |
| Mannitol 1.5 mg/kg (n = 6) | 61.8 ± 32.6 *** | 3.4 ± 0.6 *** |
| Saccharin 1.5 mg/kg (n = 3) | 84.0 ± 41.4 | 2.8 ± 1.5 ** |
| Puerarin 2.5 mg/kg (n = 6) | 89.4 ± 49.1 * | 6.7 ± 2.7 |
| Hesperitin 2.5 mg/kg (n = 6) | 67.8 ± 16.6 *** | 3.7 ± 0.7 ** |
| Combinations of two test compounds | | |
| Saccharin + Mannitol 1.5 mg/kg + 1.5 mg/kg (n = 6) | 71.6 ± 32.0 *** | 8.5 ± 2.5 |
| Menthol + Mannitol 4.5 mg/kg + 4.5 mg/kg (n = 6) | 54.3 ± 11.8 *** | |
| Menthol + Mannitol 1.5 mg/kg + 1.5 mg/kg (n = 6) | 31.0 ± 11.2 *** | 6.9 ± 1.7 |
| Menthol + Mannitol .5 mg/kg + .5 mg/kg (n = 6) | 96.6 ± 77.4 | 5.9 ± 1.7 |
| Combinations of three test compounds | | |
| Menthol + Mannitol + Eriodictyol .5 mg/kg + .5 mg/kg + .8 mg/kg (n = 6) | 83.1 ± 50.9 * | 6.0 ± 2.3 |

Data were expressed as means ± SD.

Statistical difference resulted from ANOVA and LSD was denoted by words.

* $p < 0.05$,

** $p < 0.01$,

*** $p < 0.005$, as compared with HFD.

Hesperitin

Puerarin

Eriodictyol

Phloridzin

Mannitol

Menthol

Sucralose

Saccharin

TG: triglyceride

TC: total cholesterol

TABLE 8-2

Test compounds could reduce liver lipids in
animals (administration period of 8 weeks)

| Items<br>Unit | TG in liver<br>mg/g liver | TC in liver<br>mg/g liver |
|---|---|---|
| Blank (n = 7) | 22.6 ± 3.8 *** | 3.8 ± 0.4 *** |
| HFD (n = 8) | 187.3 ± 91.2 | 12.1 ± 7.3 |
| Combinations of two test compounds | | |
| Sucralose + Mannitol<br>7.5 mg/kg + 7.5 mg/kg (n = 5) | 115.3 ± 36.2 * | 6.0 ± 3.0 ** |
| Sucralose + Mannitol<br>1.5 mg/kg + 1.5 mg/kg (n = 5) | 144.4 ± 59.9 | 6.0 ± 1.2 * |
| Eriodictyol + Mannitol<br>5.0 mg/kg + 7.5 mg/kg (n = 4) | 64.5 ± 35.7 *** | 3.6 ± 1.1 *** |
| Eriodictyol + Sucralose<br>5.0 mg/kg + 7.5 mg/kg (n = 6) | 41.1 ± 28.1 *** | 2.8 ± 1.0 *** |
| Combinations of three test compounds | | |
| Sucralose + Mannitol + Eriodictyol<br>7.5 mg/kg + 7.5 mg/kg + 2.5 mg/kg (n = 6) | 39.7 ± 21.5 * | 4.6 ± 0.6 *** |

Data were expressed as means ± SD.
Statistical difference resulted from ANOVA and LSD was denoted by words.
* $p < 0.05$,
** $p < 0.01$,
*** $p < 0.005$, as compared with HFD.
Eriodictyol
Mannitol
Sucralose
TG: triglyceride
TC: total cholesterol The results showed that TG and TC increased in liver of mice induced with fatty liver. Among the test compounds administered separately, hesperitin, puerarin, eriodictyol, phloridzin, mannitol, menthol, and sucralose could reduce TG in liver significantly. In particular, an excellent effect of about 67% reduction in liver TG content ($p<0.005$) was achieved after 4-week treatment of eriodictyol. In addition, hesperitin, eriodictyol, phloridzin, mannitol, menthol, sucralose, and saccharin could reduce TC in liver significantly. Specifically, an excellent effect of about 56% reduction in liver TC content ($p<0.005$) was achieved after 4-week treatment of saccharin.

When the combination of two test compounds was administered, the combination of saccharin and mannitol, the combination of menthol and mannitol, the combination of sucralose and mannitol, the combination of eriodictyol and mannitol, or the combination of eriodictyol and sucralose could reduce liver TG significantly. In particular, an excellent effect of about 77% reduction in liver TG content ($p<0.005$) could be achieved after 4-week treatment of the combination of menthol and mannitol; and an excellent effect of about 78% reduction in liver TG content ($p<0.005$) could be achieved after 8-week treatment of the combination of eriodictyol and sucralose. In addition, the combination of sucralose and mannitol, the combination of eriodictyol and mannitol, or the combination of eriodictyol and sucralose could reduce liver TC content significantly, in which an excellent effect of about 77% reduction in liver TC content ($p<0.005$) could be achieved after 8-week treatment of the combination of eriodictyol and sucralose.

When the combination of three test compounds was administered, the combination of menthol, mannitol, and eriodictyol or the combination of sucralose, mannitol, and eriodictyol could reduce liver TG significantly. In particular, an excellent effect of about 79% reduction in liver TG content ($p<0.005$) could be achieved after 8-week treatment of the combination of sucralose, mannitol, and eriodictyol. In addition, the combination of sucralose, mannitol, and eriodictyol could reduce liver TC significantly.

6.2.2.3 The Test Compounds are Effective in Reducing Liver Damage 6.2.2.3.1 Effects of Reduction in Liver Fat and Liver Damage of Liver Tissue The results of animal experiments showed that a plurality of test compounds exhibited the efficacies of liver fat and liver tissue damage reduction during the test period of 4 weeks. FIG. 5 showed liver tissue damage of animals having fatty liver. The liver tissue damage included many large vesicular fat droplets covering liver cells near hepatic portal area (including the bile duct, portal vein, hepatic artery) and hepatocellular ballooning. By comparison, after being treated by silymarin, menthol, eriodictyol, or mannitol for 4 weeks, large vesicular fat droplets within liver cells in liver tissue section were significantly reduced. A portion of small broken droplets was still observed in mice treated with silymarin, but the liver tissue type of mice treated with menthol, eriodictyol, or mannitol was close to that of animals in Blank group, indicating mild fatty liver diseases. Furthermore, the result of NAS scoring was shown in Table 9.

TABLE 9

The test compounds could reduce the condition of liver damage in animals

| Items<br>Unit | NAS<br>mg/g liver |
|---|---|
| Blank (n = 13) | 0.7 ± 0.5 *** |
| HFD (n = 12) | 3.3 ± 1.7 |
| Positive Control | |
| Silymarin 5.0 mg/kg (n = 6) | 0.8 ± 0.4 *** |
| Silymarin 1.5 mg/kg (n = 6) | 1.5 ± 0.8 * |
| Single test compound | |
| Phloridzin 2.5 mg/kg (n = 6) | 1.8 ± 1.0 |
| Eriodictyol 5.0 mg/kg (n = 6) | |
| Eriodictyol 2.5 mg/kg (n = 6) | 1.5 ± 0.8 * |
| Eriodictyol 7.5 mg/kg (n = 6) | 1.8 ± 1.1 |
| Eriodictyol 1.5 mg/kg (n = 6) | 1.8 ± 2.0 |
| Menthol 1.5 mg/kg (n = 6) | 1.8 ± 1.6 |
| Mannitol 7.5 mg/kg (n = 6) | 1.7 ± 0.8 * |
| Mannitol 4.5 mg/kg (n = 6) | 2.7 ± 1.9 |
| Mannitol 1.5 mg/kg (n = 6) | 1.3 ± 0.8 * |
| Saccharin 1.5 mg/kg (n = 3) | |
| Puerarin 2.5 mg/kg (n = 6) | |
| Hesperitin 2.5 mg/kg (n = 6) | 1.7 ± 0.5 |
| Combinations of two test compounds | |
| Saccharin + Mannitol<br>1.5 mg/kg + 1.5 mg/kg (n = 6) | |
| Menthol + Mannitol<br>4.5 mg/kg + 4.5 mg/kg (n = 6) | 2.2 ± 1.5 |
| Menthol + Mannitol<br>1.5 mg/kg + 1.5 mg/kg (n = 6) | 0.7 ± 0.5 *** |
| Menthol + Mannitol<br>.5 mg/kg + .5 mg/kg (n = 6) | 2.5 ± 1.8 |
| Combinations of three test compounds | |
| Menthol + Mannitol + Eriodictyol<br>.5 mg/kg + .5 mg/kg + .5 mg/kg (n = 6) | 2.0 ± 1.4 |

Data were expressed as means ± SD.
Statistical difference resulted from ANOVA and LSD was denoted by words.
* $p < 0.05$,
** $p < 0.01$,
*** $p < 0.005$, as compared with HFD.
Hesperitin
Puerarin
Eriodictyol
Phloridzin
Mannitol
Menthol
Sucralose
Saccharin NAS (Nonalcoholic Fatty Liver Disease Activity Score) indicated the activity score of non-alcoholic fatty liver diseases [Hepatology. 2005 June; 41(6): 1313-21], and comprehensively evaluated the degree of steatosis, lobular inflammation, and hepatocyte ballooning. The score sheet was shown in Table 10. Higher score indicated severer liver damage.

TABLE 10

NAS Evaluation Project

| Items | Score | Degree | Definition and Description |
|---|---|---|---|
| Steatosis | 0 | <5% | Refers to amount of surface area involved by steatosis as evaluated on low to medium power examination; minimal steatosis (.5%) receives a score of 0 to avoid giving excess weight to biopsies with very little fatty change |
| | 1 | 5-33% | |
| | 2 | >33-66% | |
| | 3 | >66% | |
| Lobular inflammation | 0 | No foci | Acidophil bodies are not included in this assessment, nor is portal inflammation |
| | 1 | <2 foci/200x | |
| | 2 | 2-4 foci/200x | |
| | 3 | >4 foci/200x | |
| Hepatocyte ballooning | 0 | None | |
| | 1 | few balloon cells | The term "few" means rare but definite ballooned hepatocytes as well as cases that are diagnostically borderline. |
| | 2 | Many cells/ prominent ballooning | Most cases with prominent ballooning also had mallory's hyaline, but Mallory's hyaline is not scored separately for the NAS. |

The results showed that liver tissue damage occurred in mice induced with fatty liver (NAS increasing). Among the test compounds administered separately, eriodictyol and mannitol could reduce liver damage significantly. It is notable that when the combination of two compounds was administered, the combination of menthol and mannitol achieved an excellent effect. There was hardly any liver damage appearing. The NAS was the same with that of the Blank.

6.2.2.3.2 Effects of Reduction in Liver Dysfunction

The results of animal experiments showed that a plurality of test compounds exhibited the efficacies of liver dysfunction reduction in animals during administration period of 4 or 8 weeks. The results were showed in Table 11-1 and Table 11-2.

TABLE 11-1

Test compounds could reduce liver dysfunction in animals (administration period of 4 weeks)

| Items Unit | ALT U/L | AST U/L |
|---|---|---|
| Blank (n = 13) | 32.6 ± 16.1 *** | 112.2 ± 53.9 *** |
| HFD (n = 12) | 70.1 ± 45.2 | 156.8 ± 100.8 |
| Positive Control | | |
| Silymarin 5.0 mg/kg (n = 6) | 33.9 ± 9.3 *** | 168.1 ± 42.6 |
| Silymarin 1.5 mg/kg (n = 6) | 43.8 ± 18.7 * | 153.6 ± 62.5 |
| Single test compound | | |
| Mannitol 7.5 mg/kg (n = 6) | 25.0 ± 10.8 *** | 63.3 ± 7.7 *** |
| Mannitol 4.5 mg/kg (n = 6) | 44.5 ± 15.9 * | 107.6 ± 54.3 |
| Mannitol 1.5 mg/kg (n = 6) | 40.8 ± 11.4 * | 187.2 ± 142.1 |
| Sucralose 7.5 mg/kg (n = 6) | 32.3 ± 10.1 ** | 74.3 ± 18.6 ** |
| Sucralose 1.5 mg/kg (n = 6) | 30.9 ± 16.8 *** | 127.0 ± 31.2 |
| Eriodictyol 5.0 mg/kg (n = 5) | 41.4 ± 6.3 * | 161.4 ± 42.3 |
| Eriodictyol 2.5 mg/kg (n = 6) | 33.7 ± 18.5 *** | 100.9 ± 42.0 |
| Puerarin 2.5 mg/kg (n = 6) | 34.4 ± 14.7 *** | 66.9 ± 8.5 *** |
| Phloridzin 2.5 mg/kg (n = 6) | 35.7 ± 9.1 *** | 161.9 ± 96.2 |
| Hesperitin 2.5 mg/kg (n = 6) | 36.8 ± 22.1 ** | 72.4 ± 11.2 *** |
| Menthol 1.5 mg/kg (n = 6) | 41.5 ± 13.7 * | 129.9 ± 37.1 |
| Saccharin 1.5 mg/kg (n = 3) | 50.7 ± 29.7 | 170.4 ± 28.6 |
| Combinations of two test compounds | | |
| Menthol + Mannitol .5 mg/kg + .5 mg/kg (n = 6) | 23.9 ± 17.8 *** | 60.4 ± 8.2 *** |
| Menthol + Mannitol 1.5 mg/kg + 1.5 mg/kg (n = 6) | 16.7 ± 4.3 *** | 59.8 ± 7.5 *** |
| Sucralose + Mannitol 7.5 mg/kg + 7.5 mg/kg (n = 6) | 45.5 ± 15.2 | 91.4 ± 21.8 * |
| Sucralose + Mannitol 1.5 mg/kg + 1.5 mg/kg (n = 6) | 52.4 ± 34.0 | 92.1 ± 23.0 * |
| Eriodictyol + Mannitol 5.0 mg/kg + 7.5 mg/kg (n = 4) | 43.4 ± 10.5 | 151.0 ± 54.2 |
| Eriodictyol + Sucralose 5.0 mg/kg + 7.5 mg/kg (n = 4) | 38.2 ± 10.9 * | 143.8 ± 67.6 |
| Saccharin + Mannitol 1.5 mg/kg + 1.5 mg/kg (n = 6) | 51.7 ± 54.2 | 70.0 ± 27.6 *** |
| Combinations of three test compounds | | |
| Menthol + Mannitol + Eriodictyol .5 mg/kg + .5 mg/kg + .8 mg/kg (n = 6) | 21.2 ± 8.7 *** | 54.8 ± 13.2 *** |

Data were expressed as means ± SD.
Statistical difference resulted from ANOVA and LSD was denoted by words.
* $p < 0.05$,
** $p < 0.01$,
*** $p < 0.005$, as compared with HFD.
Hesperitin
Puerarin
Hesperitin
Puerarin
Eriodictyol
Phloridzin
Mannitol
Menthol
Sucralose
Saccharin
ALT: alanine aminotransferase
AST: aspartate transaminase

TABLE 11-2

Test compounds could reduce liver dysfunction
in animals (administration period of 8 weeks)

| Items<br>Unit | ALT<br>U/L | AST<br>U/L |
|---|---|---|
| Blank (n = 7) | 65.1 ± 21.5 *** | 22.6 ± 4.3 *** |
| HFD (n = 8) | 111.0 ± 26.2 | 109.4 ± 46.4 |
| Combinations of two test compounds | | |
| Sucralose + Mannitol<br>7.5 mg/kg + 7.5 mg/kg (n = 5) | 92.4 ± 16.5 | 49.5 ± 14.4 *** |
| Sucralose + Mannitol<br>1.5 mg/kg + 1.5 mg/kg (n = 4) | 112.5 ± 23.8 | 93.0 ± 26.0 |
| Combinations of three test compounds | | |
| Sucralose + Mannitol + Eriodictyol<br>7.5 mg/kg + 7.5 mg/kg + 2.5 mg/kg (n = 6) | | 40.0 ± 12.2 *** |

Data were expressed as means ± SD.
Statistical difference resulted from ANOVA and LSD was denoted by words.
* $p < 0.05$,
** $p < 0.01$,
*** $p < 0.005$, as compared with HFD.
Mannitol
Sucralose
ALT: alanine aminotransferase
AST: aspartate transaminase ALT and AST are most commonly used as enzyme indicators to reflect the biochemical dysfunction of liver. Under normal circumstances, these enzymes present in liver cells. However, when liver cells are damaged, they will leak. Increases of scrum ALT and AST values generally reflect liver inflammation and liver dysfunction.

The results showed that animals induced with fatty liver (ALT and AST values increasing) suffered from liver dysfunction. Among the test compounds administered separately, all the hesperitin, puerarin, eriodictyol, phloridzin, mannitol, menthol, sucralose, and saccharin could reduce ALT and AST values significantly. In particular, excellent effects of about 64% reduction in ALT value (p<0.005) and about 60% reduction in AST value (p<0.005) could be achieved after 4-week treatment of mannitol.

When the combination of two test compounds was administered, both the combination of menthol and mannitol, and the combination of eriodictyol and sucralose could reduce ALT value significantly. Also, the combination of menthol and mannitol, the combination of sucralose and mannitol, or the combination of saccharin and mannitol could reduce AST value significantly. In particular, excellent effects of about 76% reduction in ALT value (p<0.005) and about 62% reduction in AST value (p<0.005) could be achieved after 4-week treatment of the combination of menthol and mannitol.

When the combination of three test compounds was administered, the combination of sucralose, mannitol, and eriodictyol could reduce ALT value significantly (p<0.005).

6.2.2.4 the Test Compounds can Improve Liver Antioxidant Activity

The results of animal experiments showed that a plurality of test compounds exhibited the efficacies of liver antioxidant activity improvement in animals during the test period of 4 weeks. The results were showed in Table 12-1 and Table 12-2.

TABLE 12-1

Test compounds could improve liver antioxidant
activity in animals (Gpx and GSH)

| Items<br>Unit | Gpx<br>U/L | GSH<br>U/L |
|---|---|---|
| Blank (n = 10) | 2588.0 ± 524.5 | 1224.1 ± 95.5 |
| HFD (n = 8) | 2252.5 ± 395.2 | 1193.0 ± 203.8 |
| Positive Control | | |
| Silymarin 5.0 mg/kg (n = 6) | 3358.3 ± 1205.3 *** | 1398.8 ± 396.5 |
| Single test compound | | |
| Mannitol 7.5 mg/kg (n = 6) | 3738.3 ± 665.1 *** | 2147.7 ± 459.1 *** |
| Mannitol 4.5 mg/kg (n = 6) | 3423.3 ± 547.8 *** | 1605.1 ± 305.9 ** |
| Mannitol 1.5 mg/kg (n = 6) | 2580.0 ± 555.2 | 1502.5 ± 276.9 * |
| Puerarin 2.5 mg/kg (n = 6) | 3581.7 ± 1056.7 *** | 1498.1 ± 150.0 * |
| Sucralose 7.5 mg/kg (n = 6) | 3334.0 ± 377.7 ** | 1609.1 ± 201.1 ** |
| Sucralose 1.5 mg/kg (n = 6) | 2995.0 ± 651.1 * | 1448.0 ± 281.5 |
| Phloridzin 2.5 mg/kg (n = 6) | 3234.0 ± 505.1 ** | 1387.7 ± 168.2 |
| Hesperitin 2.5 mg/kg (n = 6) | 3133.3 ± 376.9 * | 1742.6 ± 241.5 *** |

TABLE 12-1-continued

| | Test compounds could improve liver antioxidant activity in animals (Gpx and GSH) | |
|---|---|---|
| Items | Gpx | GSH |
| Unit | U/L | U/L |
| Eriodictyol 2.5 mg/kg (n = 6) | 3083.3 ± 378.9 ** | 1302.0 ± 241.1 |
| Menthol 1.5 mg/kg (n = 6) | 2921.7 ± 640.2 | 1432.7 ± 104.0 |

Data were expressed as means ± SD.
Statistical difference resulted from ANOVA and LSD was denoted by words.
* $p < 0.05$,
** $p < 0.01$,
*** $p < 0.005$, as compared with HFD.
Hesperitin
Puerarin
Hesperitin
Puerarin
Eriodictyol
Phloridzin
Mannitol
Menthol
Sucralose
Gpx: glutathione peroxidase
GSH: glutathione

TABLE 12-2

| | Test compounds could improve liver antioxidant activity in animals (Grd and SOD) | |
|---|---|---|
| Items | Grd | SOD |
| Unit | U/L | U/L |
| Blank (n = 10) | 123.5 ± 30.9 | 380.3 ± 38.8 |
| HFD (n = 8) | 82.1 ± 21.7 | 371.7 ± 49.3 |
| Positive Control | | |
| Silymarin 5.0 mg/kg (n = 6) | 88.9 ± 29.2 | 435.9 ± 59.2 * |
| Single test compound | | |
| Mannitol 7.5 mg/kg (n = 6) | 117.6 ± 32.0 ** | 462.8 ± 52.8 |
| Mannitol 4.5 mg/kg (n = 6) | 110.1 ± 18.4 * | 429.2 ± 85.2 |
| Mannitol 1.5 mg/kg (n = 6) | 95.3 ± 22.1 | 367.3 ± 35.6 |
| Puerarin 2.5 mg/kg (n = 6) | 99.0 ± 17.2 | 434.5 ± 59.8 |
| Sucralose 7.5 mg/kg (n = 6) | 90.4 ± 17.2 | 399.0 ± 34.5 |
| Sucralose 1.5 mg/kg (n = 6) | 100.0 ± 18.6 | 373.0 ± 50.4 |
| Phloridzin 2.5 mg/kg (n = 6) | 82.2 ± 33.6 | 411.5 ± 87.5 |
| Hesperitin 2.5 mg/kg (n = 6) | 102.5 ± 28.3 | 408.3 ± 66.7 |
| Eriodictyol 2.5 mg/kg (n = 6) | 86.9 ± 15.7 | 385.9 ± 34.0 |
| Menthol 1.5 mg/kg (n = 6) | 95.2 ± 16.2 | 427.9 ± 41.9 |

Data were expressed as means ± SD.
Statistical difference resulted from ANOVA and LSD was denoted by words.
* $p < 0.05$,
** $p < 0.01$,
*** $p < 0.005$, as compared with HFD.
Hesperitin
Puerarin
Hesperitin
Puerarin
Eriodictyol
Phloridzin
Mannitol
Menthol
Sucralose
Grd: Glutathione reductase
SOD: Superoxide dismutase Gpx, GSH, Grd and SOD are common members of liver antioxidant systems that can reduce oxidative stress in the liver and prevent liver from damage caused by oxidative stress. Increases of Gpx, GSH, Grd and SOD values indicate liver maintaining better antioxidant activity.

The results showed that the antioxidant activity of mice induced with fatty liver was reduced. Among the test compounds administered separately, all the hesperitin, puerarin, eriodictyol, phloridzin, mannitol, and sucralose could improve antioxidant activity significantly. In particular, excellent effects of substantial increases in Gpx, GSH, Grd, and SOD levels ($p<0.005$) were achieved after 4-week treatment of mannitol.

In summary, the compounds as tested including mannitol and sucralose and others can reduce fat content in the liver, reduce liver damage, and improve liver antioxidant activity. These compounds had been confirmed safe through animal experiments and found having potential to be developed into health food or drugs for reducing liver fat and ameliorating associated disorders, such as fatty liver diseases, acute and chronic alcoholic fatty liver diseases, acute and chronic non-alcoholic fatty liver diseases (NAFLD), acute and chronic alcoholic hepatitis, acute and chronic non-alcoholic steatohepatitis, non-alcoholic cirrhosis, and alcoholic cirrhosis (ICD-9-CM diagnosis Codes: 571.8, 571.0, 571.1, 571.2, 571.3, 571.4, 571.5, 571.9).

What is claimed is:

1. A compound represented by Formula (II):

Formula (II)

or a pharmaceutically acceptable salt or stereoisomer thereof,
wherein:
(i) $R_1$ is hydrogen;
$R_2$ is a saccharide group represented by Formula (Ia):

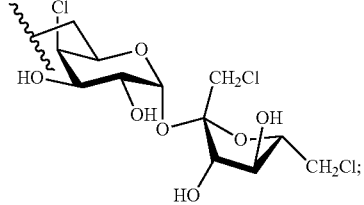

Formula (Ia)

each X is independently —C(=O)—; and
m is 3, 4, 5, 6, 7, 8, 9, or 10; or (ii) $R_1$ is a $C_3$-$C_{18}$ alkyl polyol represented by Formula A:

  Formula A or a stereoisomer thereof,
wherein:
  n is 1, 2, 3, 4, 5, 6, 7, 8, 9, 10, 11, 12, 13, 14, 15, or 16; and
$R_2$ is a saccharide group represented by Formula (Ia):

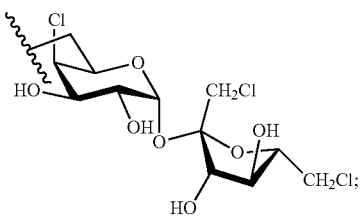  Formula (Ia)

each X is independently —C(=O)—; and
m is 3, 4, 5, 6, 7, 8, 9, or 10; or (iii) $R_1$ is a saccharide group represented by Formula (Ia):

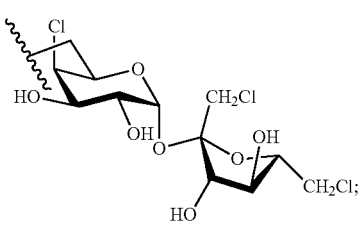  Formula (Ia)

$R_2$ is a saccharide group represented by Formula (Ia):

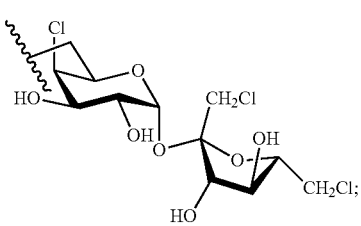  Formula (Ia)

each X is independently —C(=O)—; and
m is 3, 4, 5, 6, 7, 8, 9, or 10; or (iv) $R_1$ is hydrogen;
$R_2$ is a $C_0$-$C_{18}$ alkyl polyol represented by Formula A:

  Formula A or a stereoisomer thereof,
wherein:
  n is 2, 3, 4, 5, 6, 7, 8, 9, 10, 11, 12, 13, 14, 15, or 16;
each X is independently —C(=O)—; and
m is 3, 4, 5, 6, 7, 8, 9, or 10.

2. The compound of claim 1, or a pharmaceutically acceptable salt or stereoisomer thereof, wherein:

(i) $R_1$ is hydrogen;
$R_2$ is a saccharide group represented by Formula (Ia):

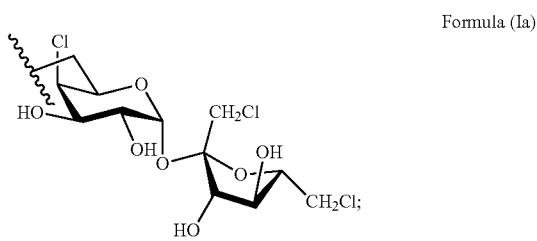  Formula (Ia)

each X is independently —C(=O)—; and
m is 3, 4, 5, 6, 7, 8, 9, or 10.

3. The compound of claim 1, or a pharmaceutically acceptable salt or stereoisomer thereof, wherein:

(ii) $R_1$ is a $C_3$-$C_{18}$ alkyl polyol represented by Formula A:

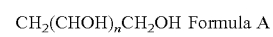 Formula A or a stereoisomer thereof,
wherein:
  n is 1, 2, 3, 4, 5, 6, 7, 8, 9, 10, 11, 12, 13, 14, 15, or 16; and
$R_2$ is a saccharide group represented by Formula (Ia):

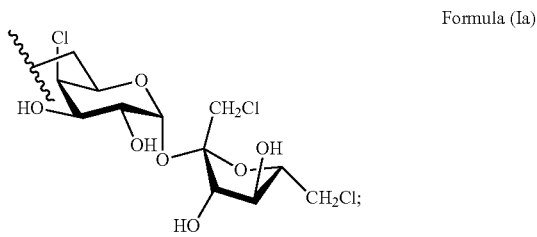  Formula (Ia)

each X is independently —C(=O)—; and
m is 3, 4, 5, 6, 7, 8, 9, or 10.

4. The compound of claim 3, or a pharmaceutically acceptable salt or stereoisomer thereof, wherein n is 2, 3, 4, 5, 6, 7, or 8.

5. The compound of claim 4, or a pharmaceutically acceptable salt or stereoisomer thereof, wherein n is 4.

6. The compound of claim 3, or a pharmaceutically acceptable salt or stereoisomer thereof, wherein Formula A is:

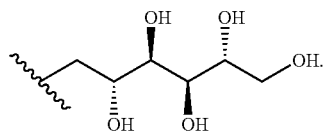 [SMILES: *C[C@@H](O)[C@@H](O)[C@H](O)[C@H](O)CO]

7. The compound of claim 1, or a pharmaceutically acceptable salt or stereoisomer thereof, wherein:

(iii) $R_1$ is a saccharide group represented by Formula (Ia):

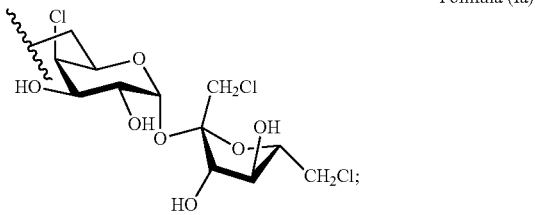

Formula (Ia)

$R_2$ is a saccharide group represented by Formula (Ia):

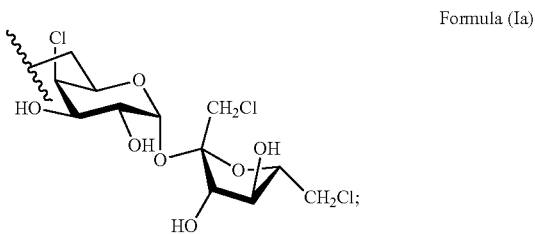

Formula (Ia)

each X is independently —C(=O)—; and
m is 3, 4, 5, 6, 7, 8, 9, or 10.

8. The compound of claim 7, or a pharmaceutically acceptable salt or stereoisomer thereof, wherein m is 4.

9. The compound of claim 1, or a pharmaceutically acceptable salt or stereoisomer thereof, wherein m is 3, 4, or 5.

10. The compound of claim 1, or a pharmaceutically acceptable salt or stereoisomer thereof, wherein:
(a) m is 4; or
(b) n is 4; or
(c) m is 4; and
n is 4.

11. The compound of claim 1, or a stereoisomer thereof, wherein the compound, or stereoisomer thereof, is:

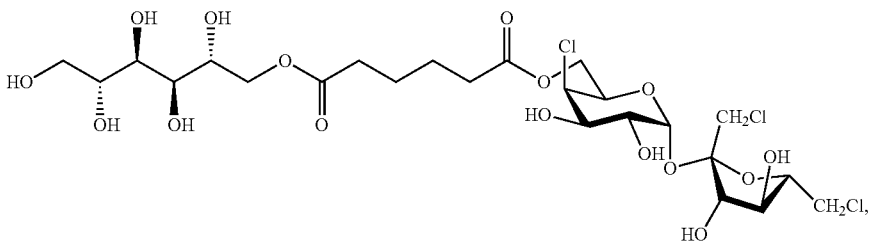

or a pharmaceutically acceptable salt thereof.

12. A pharmaceutical composition comprising a pharmaceutically acceptable carrier and the compound of claim 1, or a pharmaceutically acceptable salt or stereoisomer thereof.

13. The pharmaceutical composition of claim 12, wherein the pharmaceutical composition further comprises one or more additional agents selected from the group consisting of:
(a) a first active agent selected from the group consisting of acesulfame potassium, citric acid, croscarmellose sodium, crospovidone, dicalcium phosphate dihydrate, glycerin monostearate, glyceryl behenate, hydroxypropyl cellulose, hydroxyethyl methylcellulose, hydroxypropyl methylcellulose, lactose monohydrate, lemon oil, magnesium stearate, maltodextrin, mannitol, menthol, methylcellulose, microcrystalline cellulose, oxide red, N-acetylcysteine, pregelatinized starch, saccharin, sodium benzoate, sodium cyclamate, sodium lauryl sulfate, sodium starch glycolate, sorbic acid, sorbitol, starch acetate, sucralose, Aerosil 200, Brij 35, Brij 58, Brij 76, Copovidone K28, Cremophor EL, Cremophor RH 40, hydrated Dextrates NF, Eudragit S100, Myrj 52, PEG 400, PEG 2000, PEG 4000, PEG 8000, Pluronic F68, Povidone K30, Span 60, Span 80, Tween 20, Tween 40, and Tween 80, or any combination thereof;
(b) a second active agent selected from the group consisting of baicalein, baicalin, butylated hydroxyanisole, (+)-catechin, citric acid, didymin, diosmin, eicosapentaenoic acid, (−)-epicatechin, (−)-epicatechin-3-gallate, (−)-epigallocatechin, ergosterol, eriodictyol, formononetin, galangin, glycerin, glycyrrhizin, gossypin, hesperidin, hesperitin, hyperoside, isovitexin, kaempferol, lemon oil, (+)-limonene, linarin, luteolin, luteolin-7-glucoside, mannitol, menthol, morin, beta-myrcene, myristic acid ethyl ester, naringin, neohesperidin, nordihydroguaiaretic acid, oxide red, phloridzin, poncirin, povidone K-30, pregelatinized starch, protocatechuic acid, puerarin, quercitrin, saccharin, sciadopitysin, silybin, silymarin, sinensetin, sodium benzoate, sodium cyclamate, sodium lauryl sulfate, sorbic acid, sorbitol, swertiamarin, sucralose, (+)-taxifolin, trans-cinnamic acid, umbelliferone, ursolic acid, wongonin, and xylitol, or any combination thereof; and
(c) any combination of (a) and (b).

14. The pharmaceutical composition of claim 12, wherein the pharmaceutical composition further comprises one or more additional agents selected from the group consisting of dicalcium phosphate dihydrate, mannitol, menthol, N-acetylcysteine, and sucralose, or any combination thereof.

15. The pharmaceutical composition of claim 12, wherein the pharmaceutical composition further comprises one or more additional agents selected from the group consisting of:
(a) a combination of mannitol and saccharin;
(b) a combination of mannitol and menthol;
(c) a combination of mannitol and sucralose;
(d) a combination of mannitol and eriodictyol;
(e) a combination of eriodictyol and sucralose;
(f) a combination of eriodictyol, mannitol, and menthol; and
(g) a combination of eriodictyol, mannitol, and sucralose.

16. A method for treating an organ injury in a subject in need thereof, wherein the method comprises administering to the subject a therapeutically effective amount of a compound of claim 1, or a pharmaceutically acceptable salt or stereoisomer thereof.

17. The method of claim 16, wherein the organ injury is a kidney injury or a liver injury.

18. The method of claim 16, wherein the organ injury is caused by carbon tetrachloride, a lipid, or a therapeutic drug.

19. The method of claim 18, wherein the therapeutic drug is acetaminophen.

20. The method of claim 16, wherein the compound, or pharmaceutically acceptable salt or stereoisomer thereof, is administered in combination with one or more additional agents selected from the group consisting of:
- (a) a first active agent selected from the group consisting of acesulfame potassium, citric acid, croscarmellose sodium, crospovidone, dicalcium phosphate dihydrate, glycerin monostearate, glyceryl behenate, hydroxypropyl cellulose, hydroxyethyl methylcellulose, hydroxypropyl methylcellulose, lactose monohydrate, lemon oil, magnesium stearate, maltodextrin, mannitol, menthol, methylcellulose, microcrystalline cellulose, oxide red, N-acetylcysteine, pregelatinized starch, saccharin, sodium benzoate, sodium cyclamate, sodium lauryl sulfate, sodium starch glycolate, sorbic acid, sorbitol, starch acetate, sucralose, Aerosil 200, Brij 35, Brij 58, Brij 76, Copovidone K28, Cremophor EL, Cremophor RH 40, hydrated Dextrates NF, Eudragit S100, Myrj 52, PEG 400, PEG 2000, PEG 4000, PEG 8000, Pluronic F68, Povidone K30, Span 60, Span 80, Tween 20, Tween 40, and Tween 80, or any combination thereof;
- (b) a second active agent selected from the group consisting of baicalein, baicalin, butylated hydroxyanisole, (+)-catechin, citric acid, didymin, diosmin, eicosapentaenoic acid, (−)-epicatechin, (−)-epicatechin-3-gallate, (−)-epigallocatechin, ergosterol, eriodictyol, formononetin, galangin, glycerin, glycyrrhizin, gossypin, hesperidin, hesperitin, hyperoside, isovitexin, kaempferol, lemon oil, (+)-limonene, linarin, luteolin, luteolin-7-glucoside, mannitol, menthol, morin, beta-myrcene, myristic acid ethyl ester, naringin, neohesperidin, nordihydroguaiaretic acid, oxide red, phloridzin, poncirin, povidone K-30, pregelatinized starch, protocatechuic acid, puerarin, quercitrin, saccharin, sciadopitysin, silybin, silymarin, sinensetin, sodium benzoate, sodium cyclamate, sodium lauryl sulfate, sorbic acid, sorbitol, swertiamarin, sucralose, (+)-taxifolin, trans-cinnamic acid, umbelliferone, ursolic acid, wongonin, and xylitol, or any combination thereof; and
- (c) any combination of (a) and (b).

21. The method of claim 20, wherein the one or more additional agents are selected from the group consisting of dicalcium phosphate dihydrate, mannitol, menthol, N-acetylcysteine, and sucralose, or any combination thereof.

22. The method of claim 20, wherein the one or more additional agents are selected from the group consisting of:
- (a) a combination of mannitol and saccharin;
- (b) a combination of mannitol and menthol;
- (c) a combination of mannitol and sucralose;
- (d) a combination of mannitol and eriodictyol;
- (e) a combination of eriodictyol and sucralose;
- (f) a combination of eriodictyol, mannitol, and menthol; and
- (g) a combination of eriodictyol, mannitol, and sucralose.

23. The method of claim 20, wherein the compound, or pharmaceutically acceptable salt or stereoisomer thereof, and the one or more additional agents are administered simultaneously or sequentially.

24. A method for ameliorating a liver disease in a subject in need thereof, wherein the method comprises administering to the subject a therapeutically effective amount of a compound of claim 1, or a pharmaceutically acceptable salt or stereoisomer thereof;
wherein the liver disease is caused by fatty liver or a disorder associated with fatty liver.

25. The method of claim 24, wherein the compound, or pharmaceutically acceptable salt or stereoisomer thereof, is administered in combination with one or more additional agents selected from the group consisting of:
- (a) a first active agent selected from the group consisting of acesulfame potassium, citric acid, croscarmellose sodium, crospovidone, dicalcium phosphate dihydrate, glycerin monostearate, glyceryl behenate, hydroxypropyl cellulose, hydroxyethyl methylcellulose, hydroxypropyl methylcellulose, lactose monohydrate, lemon oil, magnesium stearate, maltodextrin, mannitol, menthol, methylcellulose, microcrystalline cellulose, oxide red, N-acetylcysteine, pregelatinized starch, saccharin, sodium benzoate, sodium cyclamate, sodium lauryl sulfate, sodium starch glycolate, sorbic acid, sorbitol, starch acetate, sucralose, Aerosil 200, Brij 35, Brij 58, Brij 76, Copovidone K28, Cremophor EL, Cremophor RH 40, hydrated Dextrates NF, Eudragit S100, Myrj 52, PEG 400, PEG 2000, PEG 4000, PEG 8000, Pluronic F68, Povidone K30, Span 60, Span 80, Tween 20, Tween 40, and Tween 80, or any combination thereof;
- (b) a second active agent selected from the group consisting of baicalein, baicalin, butylated hydroxyanisole, (+)-catechin, citric acid, didymin, diosmin, eicosapentaenoic acid, (−)-epicatechin, (−)-epicatechin-3-gallate, (−)-epigallocatechin, ergosterol, eriodictyol, formononetin, galangin, glycerin, glycyrrhizin, gossypin, hesperidin, hesperitin, hyperoside, isovitexin, kaempferol, lemon oil, (+)-limonene, linarin, luteolin, luteolin-7-glucoside, mannitol, menthol, morin, beta-myrcene, myristic acid ethyl ester, naringin, neohesperidin, nordihydroguaiaretic acid, oxide red, phloridzin, poncirin, povidone K-30, pregelatinized starch, protocatechuic acid, puerarin, quercitrin, saccharin, sciadopitysin, silybin, silymarin, sinensetin, sodium benzoate, sodium cyclamate, sodium lauryl sulfate, sorbic acid, sorbitol, swertiamarin, sucralose, (+)-taxifolin, trans-cinnamic acid, umbelliferone, ursolic acid, wongonin, and xylitol, or any combination thereof; and
- (c) any combination of (a) and (b).

26. The method of claim 25, wherein the one or more additional agents are selected from the group consisting of dicalcium phosphate dihydrate, mannitol, menthol, N-acetylcysteine, and sucralose, or any combination thereof.

27. The method of claim 25, wherein the one or more additional agents are selected from the group consisting of:
- (a) a combination of mannitol and saccharin;
- (b) a combination of mannitol and menthol;
- (c) a combination of mannitol and sucralose;
- (d) a combination of mannitol and eriodictyol;
- (e) a combination of eriodictyol and sucralose;
- (f) a combination of eriodictyol, mannitol, and menthol; and
- (g) a combination of eriodictyol, mannitol, and sucralose.

28. The method of claim 25, wherein the compound, or pharmaceutically acceptable salt or stereoisomer thereof, and the one or more additional agents are administered simultaneously or sequentially.

29. A method for treating fatty liver in a subject in need thereof, wherein the method comprises administering to the subject a therapeutically effective amount of a compound of claim 1, or a pharmaceutically acceptable salt or stereoisomer thereof.

30. The method of claim 29, wherein the compound, or pharmaceutically acceptable salt or stereoisomer thereof, is administered in combination with one or more additional agents selected from the group consisting of:
(a) a first active agent selected from the group consisting of acesulfame potassium, citric acid, croscarmellose sodium, crospovidone, dicalcium phosphate dihydrate, glycerin monostearate, glyceryl behenate, hydroxypropyl cellulose, hydroxyethyl methylcellulose, hydroxypropyl methylcellulose, lactose monohydrate, lemon oil, magnesium stearate, maltodextrin, mannitol, menthol, methylcellulose, microcrystalline cellulose, oxide red, N-acetylcysteine, pregelatinized starch, saccharin, sodium benzoate, sodium cyclamate, sodium lauryl sulfate, sodium starch glycolate, sorbic acid, sorbitol, starch acetate, sucralose, Aerosil 200, Brij 35, Brij 58, Brij 76, Copovidone K28, Cremophor EL, Cremophor RH 40, hydrated Dextrates NF, Eudragit S100, Myrj 52, PEG 400, PEG 2000, PEG 4000, PEG 8000, Pluronic F68, Povidone K30, Span 60, Span 80, Tween 20, Tween 40, and Tween 80, or any combination thereof;
(b) a second active agent selected from the group consisting of baicalein, baicalin, butylated hydroxyanisole, (+)-catechin, citric acid, didymin, diosmin, eicosapentaenoic acid, (−)-epicatechin, (−)-epicatechin-3-gallate, (−)-epigallocatechin, ergosterol, eriodictyol, formononetin, galangin, glycerin, glycyrrhizin, gossypin, hesperidin, hesperitin, hyperoside, isovitexin, kaempferol, lemon oil, (+)-limonene, linarin, luteolin, luteolin-7-glucoside, mannitol, menthol, morin, beta-myrcene, myristic acid ethyl ester, naringin, neohesperidin, nordihydroguaiaretic acid, oxide red, phloridzin, poncirin, povidone K-30, pregelatinized starch, protocatechuic acid, puerarin, quercitrin, saccharin, sciadopitysin, silybin, silymarin, sinensetin, sodium benzoate, sodium cyclamate, sodium lauryl sulfate, sorbic acid, sorbitol, swertiamarin, sucralose, (+)-taxifolin, trans-cinnamic acid, umbelliferone, ursolic acid, wongonin, and xylitol, or any combination thereof; and
(c) any combination of (a) and (b).

31. The method of claim 30, wherein the one or more additional agents are selected from the group consisting of dicalcium phosphate dihydrate, mannitol, menthol, N-acetylcysteine, and sucralose, or any combination thereof.

32. The method of claim 30, wherein the one or more additional agents are selected from the group consisting of:
(a) a combination of mannitol and saccharin;
(b) a combination of mannitol and menthol;
(c) a combination of mannitol and sucralose;
(d) a combination of mannitol and eriodictyol;
(e) a combination of eriodictyol and sucralose;
(f) a combination of eriodictyol, mannitol, and menthol; and
(g) a combination of eriodictyol, mannitol, and sucralose.

33. The method of claim 30, wherein the compound, or pharmaceutically acceptable salt or stereoisomer thereof, and the one or more additional agents are administered simultaneously or sequentially.

34. A method for treating hepatotoxicity in a subject in need thereof, wherein the method comprises administering to the subject a therapeutically effective amount of a compound of claim 1, or a pharmaceutically acceptable salt or stereoisomer thereof.

35. The method of claim 34, wherein the hepatotoxicity is caused by carbon tetrachloride, a lipid, or a therapeutic drug.

36. The method of claim 35, wherein the therapeutic drug is acetaminophen.

37. The method of claim 34, wherein the compound, or pharmaceutically acceptable salt or stereoisomer thereof, is administered in combination with one or more additional agents selected from the group consisting of:
(a) a first active agent selected from the group consisting of acesulfame potassium, citric acid, croscarmellose sodium, crospovidone, dicalcium phosphate dihydrate, glycerin monostearate, glyceryl behenate, hydroxypropyl cellulose, hydroxyethyl methylcellulose, hydroxypropyl methylcellulose, lactose monohydrate, lemon oil, magnesium stearate, maltodextrin, mannitol, menthol, methylcellulose, microcrystalline cellulose, oxide red, N-acetylcysteine, pregelatinized starch, saccharin, sodium benzoate, sodium cyclamate, sodium lauryl sulfate, sodium starch glycolate, sorbic acid, sorbitol, starch acetate, sucralose, Aerosil 200, Brij 35, Brij 58, Brij 76, Copovidone K28, Cremophor EL, Cremophor RH 40, hydrated Dextrates NF, Eudragit S100, Myrj 52, PEG 400, PEG 2000, PEG 4000, PEG 8000, Pluronic F68, Povidone K30, Span 60, Span 80, Tween 20, Tween 40, and Tween 80, or any combination thereof;
(b) a second active agent selected from the group consisting of baicalein, baicalin, butylated hydroxyanisole, (+)-catechin, citric acid, didymin, diosmin, eicosapentaenoic acid, (−)-epicatechin, (−)-epicatechin-3-gallate, (−)-epigallocatechin, ergosterol, eriodictyol, formononetin, galangin, glycerin, glycyrrhizin, gossypin, hesperidin, hesperitin, hyperoside, isovitexin, kaempferol, lemon oil, (+)-limonene, linarin, luteolin, luteolin-7-glucoside, mannitol, menthol, morin, beta-myrcene, myristic acid ethyl ester, naringin, neohesperidin, nordihydroguaiaretic acid, oxide red, phloridzin, poncirin, povidone K-30, pregelatinized starch, protocatechuic acid, puerarin, quercitrin, saccharin, sciadopitysin, silybin, silymarin, sinensetin, sodium benzoate, sodium cyclamate, sodium lauryl sulfate, sorbic acid, sorbitol, swertiamarin, sucralose, (+)-taxifolin, trans-cinnamic acid, umbelliferone, ursolic acid, wongonin, and xylitol, or any combination thereof; and
(c) any combination of (a) and (b).

38. The method of claim 37, wherein the one or more additional agents are selected from the group consisting of dicalcium phosphate dihydrate, mannitol, menthol, N-acetylcysteine, and sucralose, or any combination thereof.

39. The method of claim 37, wherein the one or more additional agents are selected from the group consisting of:
(a) a combination of mannitol and saccharin;
(b) a combination of mannitol and menthol;
(c) a combination of mannitol and sucralose;
(d) a combination of mannitol and eriodictyol;
(e) a combination of eriodictyol and sucralose;
(f) a combination of eriodictyol, mannitol, and menthol; and
(g) a combination of eriodictyol, mannitol, and sucralose.

40. The method of claim 37, wherein the compound, or pharmaceutically acceptable salt or stereoisomer thereof, and the one or more additional agents are administered simultaneously or sequentially.

41. A method for protecting liver function in a subject in need thereof, wherein the method comprises administering to the subject a therapeutically effective amount of a compound of claim 1, or a pharmaceutically acceptable salt or stereoisomer thereof.

42. The method of claim 41, wherein the compound, or pharmaceutically acceptable salt or stereoisomer thereof, is administered in combination with one or more additional agents selected from the group consisting of:
(a) a first active agent selected from the group consisting of acesulfame potassium, citric acid, croscarmellose sodium, crospovidone, dicalcium phosphate dihydrate, glycerin monostearate, glyceryl behenate, hydroxypropyl cellulose, hydroxyethyl methylcellulose, hydroxypropyl methylcellulose, lactose monohydrate, lemon oil, magnesium stearate, maltodextrin, mannitol, menthol, methylcellulose, microcrystalline cellulose, oxide red, N-acetylcysteine, pregelatinized starch, saccharin, sodium benzoate, sodium cyclamate, sodium lauryl sulfate, sodium starch glycolate, sorbic acid, sorbitol, starch acetate, sucralose, Aerosil 200, Brij 35, Brij 58, Brij 76, Copovidone K28, Cremophor EL, Cremophor RH 40, hydrated Dextrates NF, Eudragit S100, Myrj 52, PEG 400, PEG 2000, PEG 4000, PEG 8000, Pluronic F68, Povidone K30, Span 60, Span 80, Tween 20, Tween 40, and Tween 80, or any combination thereof;
(b) a second active agent selected from the group consisting of baicalein, baicalin, butylated hydroxyanisole, (+)-catechin, citric acid, didymin, diosmin, eicosapentaenoic acid, (−)-epicatechin, (−)-epicatechin-3-gallate, (−)-epigallocatechin, ergosterol, eriodictyol, formononetin, galangin, glycerin, glycyrrhizin, gossypin, hesperidin, hesperitin, hyperoside, isovitexin, kaempferol, lemon oil, (+)-limonene, linarin, luteolin, luteolin-7-glucoside, mannitol, menthol, morin, beta-myrcene, myristic acid ethyl ester, naringin, neohesperidin, nordihydroguaiaretic acid, oxide red, phloridzin, poncirin, povidone K-30, pregelatinized starch, protocatechuic acid, puerarin, quercitrin, saccharin, sciadopitysin, silybin, silymarin, sinensetin, sodium benzoate, sodium cyclamate, sodium lauryl sulfate, sorbic acid, sorbitol, swertiamarin, sucralose, (+)-taxifolin, trans-cinnamic acid, umbelliferone, ursolic acid, wongonin, and xylitol, or any combination thereof; and
(c) any combination of (a) and (b).

43. The method of claim 42, wherein the one or more additional agents are selected from the group consisting of dicalcium phosphate dihydrate, mannitol, menthol, N-acetylcysteine, and sucralose, or any combination thereof.

44. The method of claim 42, wherein the one or more additional agents are selected from the group consisting of:
(a) a combination of mannitol and saccharin;
(b) a combination of mannitol and menthol;
(c) a combination of mannitol and sucralose;
(d) a combination of mannitol and eriodictyol;
(e) a combination of eriodictyol and sucralose;
(f) a combination of eriodictyol, mannitol, and menthol; and
(g) a combination of eriodictyol, mannitol, and sucralose.

45. The method of claim 42, wherein the compound, or pharmaceutically acceptable salt or stereoisomer thereof, and the one or more additional agents are administered simultaneously or sequentially.

46. A method for reducing free radical levels in a subject in need thereof, wherein the method comprises administering to the subject a therapeutically effective amount of a compound of claim 1, or a pharmaceutically acceptable salt or stereoisomer thereof.

47. The method of claim 46, wherein the subject has a disease or condition characterized by increased free radical levels selected from the group consisting of an alcohol-related disorder, atherosclerosis, cardiovascular disease, cerebrovascular disease, cirrhosis, coronary artery disease, ethanol-induced oxidant stress, hepatitis, hepatic necrosis, hepatoblastoma, hepatocellular carcinoma, inflammation, insulin resistance, isoniazid toxicity, liver damage, a liver disease, a liver histopathology, necrosis, obesity, obesity-induced oxidant stress, poisoning, a renal disease, a renal histopathology, and tuberculosis.

48. The method of claim 47, wherein the alcohol-related disorder is alcohol abuse, alcohol withdrawal, alcoholic cirrhosis, alcoholic liver disease, or alcoholism.

49. The method of claim 47, wherein the cirrhosis is liver cirrhosis.

50. The method of claim 49, wherein the liver cirrhosis is alcoholic liver cirrhosis.

51. The method of claim 47, wherein the hepatitis is alcoholic hepatitis, chronic hepatitis, drug-induced hepatitis, halothane hepatitis, nonalcoholic steatohepatitis, or toxic hepatitis.

52. The method of claim 51, wherein the alcoholic hepatitis is acute alcoholic hepatitis.

53. The method of claim 51, wherein the chronic hepatitis is chronic hepatitis c.

54. The method of claim 47, wherein the liver damage is ethanol-induced liver injury, liver cell damage, liver fibrosis, or obesity-induced liver injury.

55. The method of claim 47, wherein the liver disease is chronic liver disease or fatty liver.

56. The method of claim 55, wherein the fatty liver is alcoholic fatty liver or fatty liver disease.

57. The method of claim 47, wherein the necrosis is liver necrosis or renal necrosis.

58. The method of claim 47, wherein the poisoning is heavy metal poisoning.

59. The method of claim 47, wherein the renal disease is chronic renal disease or renal cell damage.

60. The method of claim 46, wherein the compound, or pharmaceutically acceptable salt or stereoisomer thereof, is administered in combination with one or more additional agents selected from the group consisting of:
(a) a first active agent selected from the group consisting of acesulfame potassium, citric acid, croscarmellose sodium, crospovidone, dicalcium phosphate dihydrate, glycerin monostearate, glyceryl behenate, hydroxypropyl cellulose, hydroxyethyl methylcellulose, hydroxypropyl methylcellulose, lactose monohydrate, lemon oil, magnesium stearate, maltodextrin, mannitol, menthol, methylcellulose, microcrystalline cellulose, oxide red, N-acetylcysteine, pregelatinized starch, saccharin, sodium benzoate, sodium cyclamate, sodium lauryl sulfate, sodium starch glycolate, sorbic acid, sorbitol, starch acetate, sucralose, Aerosil 200, Brij 35, Brij 58, Brij 76, Copovidone K28, Cremophor EL, Cremophor RH 40, hydrated Dextrates NF, Eudragit S100, Myrj 52, PEG 400, PEG 2000, PEG 4000, PEG 8000, Pluronic F68, Povidone K30, Span 60, Span 80, Tween 20, Tween 40, and Tween 80, or any combination thereof;
(b) a second active agent selected from the group consisting of baicalein, baicalin, butylated hydroxyanisole, (+)-catechin, citric acid, didymin, diosmin, eicosapentaenoic acid, (−)-epicatechin, (−)-epicatechin-3-gallate, (−)-epigallocatechin, ergosterol, eriodictyol, formononetin, galangin, glycerin, glycyrrhizin, gossypin, hesperidin, hesperitin, hyperoside, isovitexin, kaempferol, lemon oil, (+)-limonene, linarin, luteolin, luteolin-7-glucoside, mannitol, menthol, morin, beta-myrcene, myristic acid ethyl ester, naringin, neohesperidin, nordihydroguaiaretic acid, oxide red, phloridzin, poncirin, povidone K-30, pregelatinized starch, protocatechuic acid, puerarin, quercitrin, saccharin, sciadopitysin, silybin, silymarin, sinensetin, sodium benzoate, sodium cyclamate, sodium lauryl sulfate, sorbic acid, sorbitol, swertiamarin, sucralose, (+)-taxifolin, trans-cinnamic acid, umbelliferone, ursolic acid, wongonin, and xylitol, or any combination thereof; and
(c) any combination of (a) and (b).

61. The method of claim 60, wherein the one or more additional agents are selected from the group consisting of dicalcium phosphate dihydrate, mannitol, menthol, N-acetylcysteine, and sucralose, or any combination thereof.

62. The method of claim 60, wherein the one or more additional agents are selected from the group consisting of:
(a) a combination of mannitol and saccharin;
(b) a combination of mannitol and menthol;
(c) a combination of mannitol and sucralose;
(d) a combination of mannitol and eriodictyol;
(e) a combination of eriodictyol and sucralose;
(f) a combination of eriodictyol, mannitol, and menthol; and
(g) a combination of eriodictyol, mannitol, and sucralose.

63. The method of claim 60, wherein the compound, or pharmaceutically acceptable salt or stereoisomer thereof, and the one or more additional agents are administered simultaneously or sequentially.

64. A method for modulating cytochrome P450 activity in a subject in need thereof, wherein the method comprises administering to the subject a therapeutically effective amount of a compound of claim 1, or a pharmaceutically acceptable salt or stereoisomer thereof.

65. The method of claim 64, wherein the subject has a disease or condition characterized by increased cytochrome P450 activity selected from the group consisting of an alcohol-related disorder, atherosclerosis, cardiovascular disease, cerebrovascular disease, cirrhosis, coronary artery disease, ethanol-induced oxidant stress, hepatitis, hepatic necrosis, hepatoblastoma, hepatocellular carcinoma, inflammation, insulin resistance, isoniazid toxicity, liver damage, a liver disease, a liver histopathology, necrosis, obesity, obesity-induced oxidant stress, poisoning, a renal disease, a renal histopathology, and tuberculosis.

66. The method of claim 65, wherein the alcohol-related disorder is alcohol abuse, alcohol withdrawal, alcoholic cirrhosis, alcoholic liver disease, or alcoholism.

67. The method of claim 65, wherein the cirrhosis is liver cirrhosis.

68. The method of claim 67, wherein the liver cirrhosis is alcoholic liver cirrhosis.

69. The method of claim 65, wherein the hepatitis is alcoholic hepatitis, chronic hepatitis, drug-induced hepatitis, halothane hepatitis, nonalcoholic steatohepatitis, or toxic hepatitis.

70. The method of claim 69, wherein the alcoholic hepatitis is acute alcoholic hepatitis.

71. The method of claim 69, wherein the chronic hepatitis is chronic hepatitis c.

72. The method of claim 65, wherein the liver damage is ethanol-induced liver injury, liver cell damage, liver fibrosis, or obesity-induced liver injury.

73. The method of claim 65, wherein the liver disease is chronic liver disease or fatty liver.

74. The method of claim 73, wherein the fatty liver is alcoholic fatty liver or fatty liver disease.

75. The method of claim 65, wherein the necrosis is liver necrosis or renal necrosis.

76. The method of claim 65, wherein the poisoning is heavy metal poisoning.

77. The method of claim 65, wherein the renal disease is chronic renal disease or renal cell damage.

78. The method of claim 64, wherein the compound, or pharmaceutically acceptable salt or stereoisomer thereof, is administered in combination with one or more additional agents selected from the group consisting of:
(a) a first active agent selected from the group consisting of acesulfame potassium, citric acid, croscarmellose sodium, crospovidone, dicalcium phosphate dihydrate, glycerin monostearate, glyceryl behenate, hydroxypropyl cellulose, hydroxyethyl methylcellulose, hydroxypropyl methylcellulose, lactose monohydrate, lemon oil, magnesium stearate, maltodextrin, mannitol, menthol, methylcellulose, microcrystalline cellulose, oxide red, N-acetylcysteine, pregelatinized starch, saccharin, sodium benzoate, sodium cyclamate, sodium lauryl sulfate, sodium starch glycolate, sorbic acid, sorbitol, starch acetate, sucralose, Aerosil 200, Brij 35, Brij 58, Brij 76, Copovidone K28, Cremophor EL, Cremophor RH 40, hydrated Dextrates NF, Eudragit S100, Myrj 52, PEG 400, PEG 2000, PEG 4000, PEG 8000, Pluronic F68, Povidone K30, Span 60, Span 80, Tween 20, Tween 40, and Tween 80, or any combination thereof;
(b) a second active agent selected from the group consisting of baicalein, baicalin, butylated hydroxyanisole, (+)-catechin, citric acid, didymin, diosmin, eicosapentaenoic acid, (−)-epicatechin, (−)-epicatechin-3-gallate, (−)-epigallocatechin, ergosterol, eriodictyol, formononetin, galangin, glycerin, glycyrrhizin, gossypin, hesperidin, hesperitin, hyperoside, isovitexin, kaempferol, lemon oil, (+)-limonene, linarin, luteolin, luteolin-7-glucoside, mannitol, menthol, morin, beta-myrcene, myristic acid ethyl ester, naringin, neohesperidin, nordihydroguaiaretic acid, oxide red, phloridzin, poncirin, povidone K-30, pregelatinized starch, protocatechuic acid, puerarin, quercitrin, saccharin, sciadopitysin, silybin, silymarin, sinensetin, sodium benzoate, sodium cyclamate, sodium lauryl sulfate, sorbic acid, sorbitol, swertiamarin, sucralose, (+)-taxifolin, trans-cinnamic acid, umbelliferone, ursolic acid, wongonin, and xylitol, or any combination thereof; and
(c) any combination of (a) and (b).

79. The method of claim 78, wherein the one or more additional agents are selected from the group consisting of dicalcium phosphate dihydrate, mannitol, menthol, N-acetylcysteine, and sucralose, or any combination thereof.

80. The method of claim 78, wherein the one or more additional agents are selected from the group consisting of:
(a) a combination of mannitol and saccharin;
(b) a combination of mannitol and menthol;
(c) a combination of mannitol and sucralose;

(d) a combination of mannitol and eriodictyol;
(e) a combination of eriodictyol and sucralose;
(f) a combination of eriodictyol, mannitol, and menthol; and
(g) a combination of eriodictyol, mannitol, and sucralose.

81. The method of claim 78, wherein the compound, or pharmaceutically acceptable salt or stereoisomer thereof, and the one or more additional agents are administered simultaneously or sequentially.

* * * * *